(12) United States Patent
Morales Molina et al.

(10) Patent No.: US 11,147,762 B2
(45) Date of Patent: Oct. 19, 2021

(54) COMPOSITION FOR USE IN THE TREATMENT OF MUCOUS MEMBRANE LESIONS USING ENDOSCOPIC RESECTION

(71) Applicants: Agencia Pública Empresarial Sanitaria Hospital de Poniente, El Ejido (ES); Universidad de Granada, Granada (ES)

(72) Inventors: José Antonio Morales Molina, El Ejido (ES); Pedro Acosta Robles, El Ejido (ES); Francisco Javier Gallego Rojo, El Ejido (ES); Beatriz Clares Naveros, Granada (ES)

(73) Assignees: Agencia Pública Empresarial Sanitaria Hospital De, El Ejido (ES); Universidad de Granada, Granada (ES)

( * ) Notice: Subject to any disclaimer, the term of this patent is extended or adjusted under 35 U.S.C. 154(b) by 53 days.

(21) Appl. No.: 16/067,912

(22) PCT Filed: Jan. 4, 2017

(86) PCT No.: PCT/ES2017/070007
§ 371 (c)(1),
(2) Date: Jul. 3, 2018

(87) PCT Pub. No.: WO2017/118774
PCT Pub. Date: Jul. 13, 2017

(65) Prior Publication Data
US 2020/0261355 A1      Aug. 20, 2020

(30) Foreign Application Priority Data
Jan. 4, 2016   (ES) ................ P201630003

(51) Int. Cl.
| A61K 9/00 | (2006.01) |
| A61K 31/137 | (2006.01) |
| A61K 47/38 | (2006.01) |
| A61B 17/00 | (2006.01) |
| A61K 47/26 | (2006.01) |

(52) U.S. Cl.
CPC ...... *A61K 9/0019* (2013.01); *A61B 17/00234* (2013.01); *A61K 31/137* (2013.01); *A61K 47/38* (2013.01); *A61B 2017/00269* (2013.01); *A61B 2017/00818* (2013.01); *A61K 47/26* (2013.01)

(58) Field of Classification Search
IPC ............... A61K 9/0019,47/38, 31/728
See application file for complete search history.

(56) References Cited

U.S. PATENT DOCUMENTS

| 10,856,551 B2 | 12/2020 | Béjar Luque et al. |
| 2003/0225460 A1 | 12/2003 | Gostout et al. |
| 2004/0241155 A1 | 12/2004 | Shah |
| 2006/0040894 A1 | 2/2006 | Hunter et al. |
| 2014/0219939 A1 | 8/2014 | Yasuda et al. |
| 2014/0221309 A1* | 8/2014 | Beard .............. A61K 31/205 514/57 |
| 2015/0099928 A1* | 4/2015 | Smith .............. A61M 5/178 600/104 |
| 2019/0004015 A1 | 1/2019 | Rus Calborg et al. |
| 2020/0215227 A1 | 7/2020 | Carriel Araya et al. |

FOREIGN PATENT DOCUMENTS

| EP | 1 992 362 A2 | 11/2008 |
| JP | 2001-192336 A | 7/2001 |
| KR | 10-2011-0057877 A | 6/2011 |
| WO | 03/074108 A2 | 9/2003 |
| WO | 2007/013100 A1 | 2/2007 |
| WO | 2014/121232 A1 | 8/2014 |
| WO | 2015/054208 A1 | 4/2015 |
| WO | 2015/075015 A1 | 5/2015 |

OTHER PUBLICATIONS

Google Scholar search_Oct. 9, 2020_mucosal lesion cellulose hyaluronate (Year: 2020).*
U.S. Appl. No. 17/092,154, filed Nov. 6, 2020.
U.S. Appl. No. 17/265,790, filed Feb. 3, 2021.
Hikichi et al., "Sa1766 Novel Injection Technique: Endoscopic Submucosal Dissection by Submucosal Injection of Sodium Carboxymethylcellulose for Early Gastric Cancer," *Gastrointestinal Endoscopy* 75(45):AB269, 2012.
Hui et al., "Endoscopic Resection With Hyaluronate Solution for Gastrointestinal Lesions: Systematic Review and Meta-Analysis," *Surg. Laparosc. Endosc. Percutan. Tech.* 24(3):193-198, 2014.
Jung et al., "Submucosal injection solutions for endoscopic mucosal resection and endoscopic submucosal dissection of gastrointestinal neoplasms," *Gastrointest. Interv.* 2:73-77, 2013.
Ono et al., "Endoscopic mucosal resection for treatment of early gastric cancer," *Gut* 48:225-229, 2001.
Pavithran et al., "Gastric cancer in India," *Gastric Cancer* 5:240-243, 2002.
Uraoka et al., "Endoscopic mucosal resection and endoscopic submucosal dissection," *Gastrointestinal Endoscopy* 68(1):11-18, 2008.

(Continued)

*Primary Examiner* — Michael P Cohen
(74) *Attorney, Agent, or Firm* — Seed IP Law Group LLP

(57) ABSTRACT

The present invention relates to a composition, preferably an aqueous pharmaceutical solution, comprising a water-soluble polymer derived from cellulose and hyaluronic acid, preferably comprising carboxymethylcellulose and hyaluronic acid. More specifically, the invention relates to a composition, preferably an aqueous pharmaceutical solution, comprising 0.0001%-5% hyaluronic acid and 0.005%-2% carboxymethylcellulose. The invention also relates to the use of said composition, preferably an aqueous pharmaceutical solution, in the manufacturing of a medicament for the treatment of lesions in the mucosa by means of endoscopic resection, for example, the resection of polyps and/or tumors of the gastrointestinal mucosa.

13 Claims, 10 Drawing Sheets

(56) References Cited

OTHER PUBLICATIONS

Uraoka et al., "Submucosal injection solution for gastrointestinal tract endoscopic mucosal resection and endoscopic submucosal dissection," *Drug Design, Development Therapy* 2:131-138, 2008.
Yamasaki et al., "A novel method of endoscopic submucosal dissection with blunt abrasion by submucosal injection of sodium carboxymethylcellulose: an animal preliminary study," *Gastrointestinal Endoscopy* 64(6): 958-965, 2006.
Kusano et al., "Evaluation Of 0.6% Sodium Alginate as an Endoscopic Submucosal Injectant for Gastric Neoplasm," *Gastroenterological Endoscopy* 56(6):2028-2037, 2014, (with English Abstract Translation).

\* cited by examiner

COMPOSITION FOR USE IN THE TREATMENT OF MUCOUS MEMBRANE LESIONS USING ENDOSCOPIC RESECTION

FIELD OF THE INVENTION

The present invention is comprised in the field of medicine and pharmacy. Said invention relates to a composition, preferably an aqueous pharmaceutical solution, comprising a polymer derived from water-soluble cellulose and hyaluronic acid, preferably comprising carboxymethylcellulose and hyaluronic acid. The invention also relates to the use of said composition, preferably aqueous pharmaceutical solution, in the manufacturing of a medicament, more specifically, for the treatment of lesions in the mucosa by means of endoscopic resection, for example, the resection of polyps and/or tumors, in the gastrointestinal tract mucosa.

BACKGROUND OF THE INVENTION

The treatment of the pre-malignant digestive (or early neoplastic) lesions has experienced an enormous change primarily brought about by the development of new endoscopes and the emergence of new endoscopic instruments. With the development of endoscopic submucosal resection (commonly referred to as mucosectomy) and endoscopic submucosal dissection, early neoplastic lesions of the gastrointestinal mucosa are endoscopically resectable, virtually in their entirety, by means of these minimally invasive techniques.

Europe, America, China, India and Japan are the areas with the highest prevalence of potentially resectable gastrointestinal tumors (Pavithran K, et al., "Gastric Cancer in India". Gastric Cancer. 2002; 5: 240-3). The use of this technique is generally accepted as a treatment option for the cases of early tumors where the probability of lymph node metastases is low. Because mucosectomy is a minimally invasive, low-cost technique in comparison with conventional surgery, and because it heals the lesion, endoscopic resection (both mucosectomy and submucosal dissection) is becoming very wide-spread in these countries (Ono H, et al., "Endoscopic mucosal resection for treatment of early gastric cancer" Gut. 2001; 2 (48):225-9). In Western society, the most popular technique is mucosectomy, which is a simpler and safer technique, that has a shorter intervention period than endoscopic submucosal dissection (more developed in Asian countries such as Japan).

For the purpose of improving resection efficiency, as well as the ease and safety of endoscopic submucosal resection operations, a lifting agent conventionally has been used, traditionally a physiological saline solution, associated with an organic dye which is commonly injected under the mucosa of the zone designated for resection, resulting in a lifting of the lesion that allows demarcating and removing the damaged tissue.

However, there are limiting factors in endoscopic resection, such as not having an ideal lifting agent or submucosal injection solution. It is sometimes difficult to precisely remove the area of the lesion using conventional agents due to, among other factors, a low degree of protuberance, and particularly due to the fact that the lifting agent immediately spreads after injection towards peripheral tissue, thereby causing the protuberance or bump to disappear before the resection process ends, which forces the surgeon to repeat the injection of the lifting agent.

One of the few products commercially available for use as a solution for submucosal injection is Glyceol® (Uraoka T, et al., "Submucosal injection solution for gastrointestinal tract endoscopic mucosal resection and endoscopic submucosal dissection". Drug Des Devel Ther. 2009; 2:131-8). The use of hypertonic solutions +/-adrenalin with the same mixing sequence but with 10% glycerol has also been described. The glycerol solution is cost-effective and easy to prepare, but its high viscosity and short-lasting effect can limit use. In addition, from a rheological viewpoint, it is a fluid with Newtonian characteristics. In addition, due to its high viscosity, it presents difficulties for being injected at the submucosal level. Furthermore, it can produce "fumes" making it difficult to carry out the technique.

Hyaluronic acid can also be used, but its high cost and viscosity when injected can limit its use (Jung YS, Park DII. "Submucosal injection solutions for endoscopic mucosal resection and endoscopic submucosal dissection of gastrointestinal neoplasms". Gastrointest Interv. 2013; 2:73-77). Hui P et al. recently reported that HA is more effective than saline solution for keeping the mucosa lifted up (Hui P, Long Z Y, Jun H X, Wei W, Yong H J, Peng L H. "Endoscopic resection with hyaluronate solution for gastrointestinal lesions: systematic review and meta-analysis" Surg Laparosc Endosc Percutan Tech. 2014; 24 (3):193-8). Additionally, patent application KR 20110057877 seems to describe a hyaluronic acid solution between 0.1 and 1% tested for use as an injectable solution in endoscopic submucosal dissection methods.

Both hyaluronic acid and hydroxypropylmethylcellulose (HPMC) are highly viscous and must often be diluted to make injection easier. Additionally, the HPMC has been associated with tissue damage and inflammation at the injection site (Uraoka T, et al., "Submucosal injection solution for gastrointestinal tract endoscopic mucosal resection and endoscopic submucosal dissection". Drug Des Devel Ther. 2008; 2:131-8); "Endoscopic mucosal resection and endoscopic submucosal dissection", Gastrointestinal endoscopy 2008, 68:1 11-18). Patent application WO 03/074108 describes the use of 0.83% HPMC for submucosal injection in mucosal resection or polypectomy interventions. Specifically, an in vivo assay is described in which the injection of said solution is performed by means of a 23G needle in two groups of animals in which alternative methods of marking the resection area have been used, resulting in mean lifting times 36 minutes and 38 minutes, respectively.

Additionally, a carboxymethylcellulose (CMC) solution at a concentration greater than 2% has been described as optimal for submucosal injection in methods of endoscopic submucosal dissection (EDS). Specifically, the submucosal injection from a 0.5% to 1.5% solution in the submucosal layer in an in vitro model did not allow separating the mucosal layer from the muscular layer. In contrast, the submucosal injection of a solution of between 2% and 3.5% of carboxymethylcellulose characterized by a viscosity of 200 mPa*S did in fact separate both layers. Based on said results, a concentration of 2.5% was selected for experimentation in an animal model. Because a CMC solution exceeding 2% is highly viscous, a special 18G needle was required to carry out said submucosal injection (Yamasaki et al. "A novel method of endoscopic submucosal dissection with blunt abrasion by submucosal injection of sodium carboxymethylcellulose: an animal preliminary study". Gastrointestinal Endoscopy 2006; 64(6), 958-965; Uraoka T, et al., "Submucosal injection solution for gastrointestinal tract endoscopic mucosal resection and endoscopic submucosal dissection". Drug Des Devel Ther. 2008; 2:131-8).

Hikichi et al. 2012 ("Novel Injection Technique: Endoscopic Submucosal Dissection by Submucosal Injection of Sodium Carboxymethylcellulose for Early Gastric Cancer"; Gastrointestinal Endoscopy, 2012, 75 (4S), Sa1765) mention a study in early-stage gastric cancer patients in which a solution of sodium carboxymethylcellulose at a concentration of 1.5% is used for endoscopic resection. Said solution was injected into the submucosal layer with a 25G needle. The mean treatment duration was 31.4 minutes from injection of the submucosal solution until the end of the procedure. However, the mean duration of the lifting is not indicated.

Combinations of CMC and hyaluronic acid have been described for other uses, for example in US 2004241155 A1 reference is made to the use of hyaluronic acid solutions with water-soluble polymers derived from cellulose and a molecular weight less than 100 kDa for use in ophthalmic or articular surgery applications, mentioning the combination of hyaluronic acid with CMC at 1%. Additionally, EP 1992362 A2 relates to compositions comprising hyaluronic acid and a preservative agent (for example, benzalkonium chloride) for ophthalmic, otic or nasal use. The use of anionic cellulose derivatives having a molecular weight between 70 and 700 kDa is mentioned.

In conclusion, there is currently a need to find a composition for use as a lifting agent in endoscopic treatments comprising resection of a portion of the gastrointestinal mucosa. Said solution must have a low cost, be readily available, and have optimal viscosity. Optimal viscosity is one which on the one hand allows it to be easy to inject, enabling the use of standard injection needles (for example, 21G, 23G or 25G), and on the other hand provides good lifting of the lesion for a prolonged time (for example, at least 45 minutes, preferably around 60 minutes or more). The endoscopic treatment duration will depend on the size of the lesion and the ideal composition will prevent the need for reinjection during the endoscopic method due to loss of consistency of the lifting (also referred to as protuberance or bump). Additionally, said composition must be non-toxic, lacking any side effects, such as tissue damage, bleeding and/or inflammation of the injection tissue, therefore allowing a safe endoscopic intervention. Finally, the ideal composition is one that allows sterilization without losing its rheological properties.

BRIEF DESCRIPTION OF THE INVENTION

The composition of the invention, preferably an aqueous pharmaceutical solution, having a mechanical-pharmacological effect, comprising hyaluronic acid and carboxymethylcellulose, was compared in Example 1 with a 10% glycerol solution produced in the pharmacy department of the hospital, both solutions further comprising: physiological saline, fructose, adrenalin and methylene blue as dye.

Twenty mucosectomies were performed, and it was observed that when the solution was introduced with the endoscope into the intestinal submucosa, a lift or bump was separating for an average of 45 minutes the zone of the lesion (e.g. tumor and/or polyp) from the zone irrigated by blood vessels, such that the damaged tissue could be precisely removed, avoiding the irrigated tissue, and the risk of hemorrhages was thereby reduced, and recovery was also faster. A solution injected into the submucosa was subsequently reabsorbed without producing adverse effects, giving sufficient time for the intervention to be performed. The advantages observed with the 10% glycerol solution were: longer permanence of the compound at the intestinal level, large expansion of the tissue injecting a minimum amount of product, optimal viscosity (injection of the product with ease), complete subsequent reabsorption of the administered product,
absence of fumes,
physicochemical stability of at least 24 h and microbiological stability of at least 30 days.

A second retrospective study (Example 2) was conducted in 10 patients subjected to colonic endoscopic mucosal resection of flat lesions ≥15 mm, with a mean size of 27 mm. When studying the composition of the invention in endoscopic methods for the resection of larger sized lesions, it was found that it was not necessary to reinject any patient due to loss of consistency of the "bump", and the solution remained in the intestinal submucosa for a mean time of 72 minutes. The generated "bump" allowed separating the mucosal layer from the muscularis "propria", being effective throughout the entire intervention, and no complications were observed during the intervention in any patient. The solution injected into the submucosa was subsequently reabsorbed, in all cases, without any problems and showing no signs of inflammation or tissue damage resulting from the solution used, neither during the intervention nor during the follow-up visits in months 1 and 3 after the performing the procedure.

In addition, in the characterization and stability studies (Example 3) it was observed that the solution of the invention, made up of carboxymethylcellulose (pseudoplastic behavior) and hyaluronic acid (Newtonian behavior), is a pseudoplastic fluid with negligible thixotropy values. This gives the solution a very stable viscosity over time.

Therefore in a first aspect, the invention relates to a composition, preferably an aqueous pharmaceutical solution, comprising:
  hyaluronic acid at a concentration from 0.0001% to 5%, and
  a water-soluble polymer derived from cellulose (for example, carboxymethylcellulose) at a concentration from 0.005% to 2%.

In a second aspect, the present invention relates to a method for obtaining a composition comprising the following steps:
  a) mixing a gel of a water-soluble polymer derived from cellulose having a viscosity of 3,000 to 5,000 mPa*s in a 2% aqueous solution with an aqueous solvent;
  b) mixing the solution obtained in step a) with hyaluronic acid; and
  c) optionally, a dye and/or one or more active ingredients or excipients is incorporated during step a) or after obtaining said composition in a).

In a third aspect, the present invention relates to a composition obtained or obtainable by a method as described in the second aspect of the invention. Preferably, said composition is a composition according to the first aspect of the invention obtained by a method according to the second aspect of the invention.

In a related aspect, the invention relates to the use of the composition (preferably pharmaceutical composition) of the invention as a carrier for the administration of compounds useful in methods of diagnostic, surgical and/or therapeutic treatment. Said compounds include active ingredients with pharmacological activity as well as radioisotopes or other compounds commonly used for diagnostic purposes.

In another additional aspect, the invention relates to the composition of the invention for use as a medicament.

In a related aspect, the invention relates to the composition of the invention for use, preferably as a lubricant, in the treatment of syndromes or diseases affecting the joints.

Additionally, the invention relates to the composition according to the first and third aspects of the invention, for use in a method of treatment requiring the separation of tissues, where said composition is administered by means of injection, preferably by means of endoscopic injection, in one of the tissues to be separated or in a tissue located between both.

In another additional aspect, the invention relates to a composition (preferably pharmaceutical solution) according to the first or third aspect of the invention, for use in manufacturing a medicinal product for treatment the treatment of lesions in the mucosa comprising resection, usually endoscopic resection, of a portion of the mucosa.

In a related aspect, the invention relates to the composition (preferably pharmaceutical solution) according to the first or third aspect of the invention for use in a method for the treatment of lesions in the mucosa, where said method comprises the resection, usually endoscopic resection, of a portion of the mucosa. Additionally, in another aspect the invention relates to a method for the treatment of lesions in the mucosa in a patient comprising the injection of a therapeutically effective amount of said solution for the resection, usually endoscopic resection, of a portion of the mucosa.

Additionally, the invention also relates to the composition of the invention for use in the treatment of lesions in the mucosa of the gastrointestinal tract. In a related aspect relates to the use of the composition of the invention in the manufacturing of a medicament for the treatment of lesions in the mucosa of the gastrointestinal tract. Finally, it also relates to a method for the treatment of lesions in the mucosa of the gastrointestinal tract, where said method comprises the injection, typically the endoscopic injection, of a therapeutically effective amount of said composition.

In an additional aspect, the invention relates to the use of the composition (preferably pharmaceutical solution) of the invention as a solution for submucosal injection or as a lifting agent in endoscopic resection procedures.

In another aspect of the invention, a kit is further provided, said kit comprising one or more containers containing the composition (preferably pharmaceutical solution) of the invention, and optionally, instructions for the use thereof in a method of treatment such as those described in the present document, preferably, for use by means of submucosal injection (preferably as a lifting agent) in a method of treatment of endoscopic resection.

DESCRIPTION OF THE INVENTION

Definitions

Figure 1:
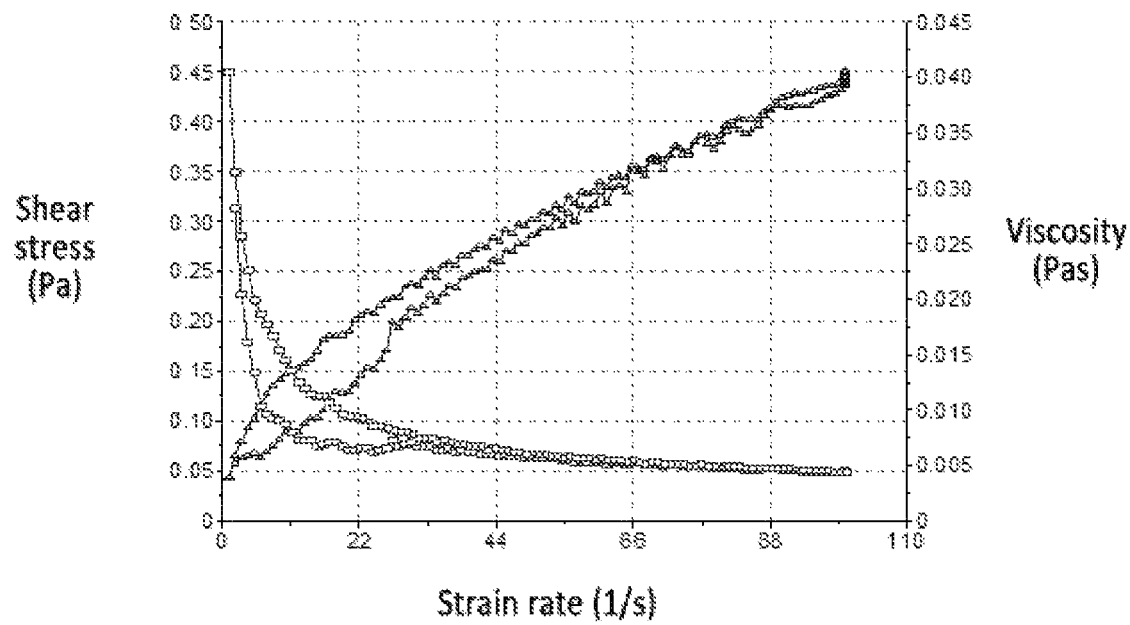
FIG. 1 shows a viscosity curve (squares) and flow curve (triangles) of Formulation 1—Sample M1502 Glycerol at time 0 (replicate 1).

As it is used herein, the term "aqueous composition" refers to a liquid or semi-solid composition (e.g. a solution, suspension or gel) containing water, optionally combined with other mutually miscible solvents (for example, water-soluble organic solvents), and one or more chemicals dissolved in it.

The term "pharmaceutical composition" relates to a composition that does not contain agents considered toxic or infectious at a concentration that is harmful for the subject to which it is administered through the suitable administration route. Preferably, said pharmaceutical composition is sterile.

As it is used herein, the term "pharmaceutically acceptable salt" refers to relatively non-toxic organic and inorganic acid addition salts of the compounds as described herein. These salts can be prepared in situ during the final isolation and purification of the compounds or by separately reacting the compound purified in its free base form with a suitable organic or inorganic acid and isolating the salt thus formed.

Representative salts include hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthilate, mesylate, glucoheptonate, lactobionate and lauryl sulfonate salts, and the like. These can include cations based on the alkaline and alkaline earth metals, such as sodium, lithium, potassium, calcium, magnesium and the like, as well as non-toxic ammonium, quaternary ammonium, and amine cations including, but without being limited to ammonium, tetramethylammonium, tetraethylammonium, methylamine, dimethylamine, trimethylamine, triethylamine, ethylamine, and the like (see, for example, Berge S. M, et al., "Pharmaceutical Salts," J. Pharm. Sci., 1977; 66:1-19 which is incorporated herein by reference).

As it is used herein, the term "therapeutically effective amount" refers to an amount that is effective after administering an individual dose of the composition of the invention to a subject.

As it is used herein, the term "subject" refers to a mammal. Preferably, the subject is selected from the group consisting of human beings, pets, non-domestic farm animals and zoo animals. For example, the subject can be selected from a human being, dog, cat, cow, pig, sheep, horse, bear, and so on and so forth. In a preferred embodiment, said mammal is a human.

As it is used herein, the term "neoplasia" or "neoplastic lesion" covers dysplasia, pre-cancerous lesions, cancerous lesions, neoplastic cells, tumors, benign tumors, malignant tumors, solid tumors, carcinomas, etc., preferably located in the skin and soft tissues of any part of the body.

As it is used herein, the term "precancerous lesion" includes syndromes represented by an abnormal neoplastic growth, including dysplastic syndromes. Non-limiting examples include, in addition to dysplastic syndromes, nevus, polyposis syndromes, intestinal polyps, pre-cancerous lesions of the cervix (i.e., cervical dysplasia), dysplasia of the prostate, bronchial dysplasia, and dysplasia of the breast and/or bladder, whether or not the lesions are clinically identifiable.

As it is used herein, the term "pseudoplastic" refers to a fluid in which the apparent viscosity or consistency decreases with an increase in the shear rate. Therefore, the decrease in viscosity of the fluid is not dependent on time, and viscosity of the fluid decreases almost instantaneously by means of applying pressure when the fluid is injected into the tissue with the endoscopic injection needle but it rapidly recovers its initial viscosity right after the pressure is released. Pseudoplasticity can be evaluated using the Casson yield value. A major Casson yield value means that viscosity at rest is higher, and therefore the lifting can be maintained for a longer period of time without diffusion. A too high Casson yield value causes a high injection pressure, which affects manageability during the injection. The Casson yield value of the pharmaceutical composition of the invention is preferably from 0.1 to 100, more preferably from 0.5 to 75, and even more preferably from 1 to 50.

The Composition of the Present Invention

A first aspect of the invention relates to a composition, preferably an aqueous composition, comprising 0.005% to 2% carboxymethylcellulose, where said composition preferably comprises:
   hyaluronic acid at a concentration from 0.0001% to 5%, and
   a water-soluble polymer derived from cellulose (for example, carboxymethylcellulose) at a concentration from 0.005% to 2%.

Preferably, said composition is an aqueous solution or hydrated gel which can be clear or cloudy. In the present invention, unless indicated otherwise, the concentrations are expressed in weight/volume.

In a preferred embodiment, optionally combined with one or more of the features of other embodiments of the invention, said (preferably aqueous) composition comprises:
   a water-soluble polymer derived from cellulose at a concentration from 0.005% to 2%, and
   hyaluronic acid at a concentration from 0.0001% to 0.5%;
   where the viscosity of said composition is from 5 to 100 mPa*s, preferably from 5 to 50 mPa*s, more preferably from 10 to 40 mPa*s. Examples of viscosities within the most preferred range are from 15 a 30 mPa*s and from 20 to 40 mPa*s.

As it is used in the invention, the term "hyaluronic acid" refers to a polysaccharide including at least one constituent unit consisting of a glucuronic acid and N-acetylglucosemine. It also includes pharmaceutically acceptable salts thereof, which are not particularly limited, and include, for example, a sodium salt, a potassium salt, a calcium salt, a zinc salt, a magnesium salt, ammonium salt, alkyl ammonium salt, and the like. The term "hyaluronic acid" also includes derivative thereof such as those described in EP2537867 A1. Preferably, said hyaluronic acid is hyaluronic acid sodium salt.

In the present invention when referring to the molecular weight of the polymers used in the invention, a person skilled in the art will understand that reference is being made to the mean molecular weight. Methods for determining the mean molecular weight are well known by a person skilled in the art and include, for example, assays using the osmotic method (membrane or vapor pressure osmometry), analysis of terminal groups, laser light scattering, sedimentation equilibrium by means of analytical ultracentrifugation, viscometry, polymer sample fractionation techniques with in-line detection: liquid size exclusion chromatography (SEC/GPC) and matrix-assisted laser desorption/ionization mass spectroscopy: (MALDI) mass spectroscopy, and combinations thereof.

The hyaluronic acid can be of high or low molecular weight. Typically, are considered hyaluronic acid of high molecular weight those chains of said polysaccharide of more than 1,000 kDa, preferably more than 1,500 kDa or 1,800 kDa. Meanwhile, those chains having a molecular weight of less than 1,000 kDa, preferably less than 800 kDa, more preferably less than 600 kDa, even more preferably less than 300 kDa or less than 250 kDa, are usually considered low-molecular weight hyaluronic acid. In a particular embodiment, the hyaluronic acid of the composition of the present invention is low molecular weight hyaluronic acid, preferably having a mean molecular weight of 500 to 800 kDa.

Likewise, the hyaluronic acid can also be defined by its viscosity. Preferably, the hyaluronic acid of the composition (preferably pharmaceutical composition) of the present invention is a low-viscosity hyaluronic acid, for example, said hyaluronic acid has a viscosity in a 1% aqueous solution from 100 to 300 mPa*s, preferably from 150 to 250 mPa*s. Mid- or high-viscosity hyaluronic acid could also be used.

The viscosity of a pharmaceutical solution is conventionally measured by means of using a viscometer. There are different types of viscometers in many applications today that have different measurement purposes. A person skilled in the art will know how to choose the most suitable viscometer, for example a rotational viscometer (also referred to as a spindle viscometer), such as Brookfield LV (for example using spindle 3 at 30 rpm) or Viscometer Haake VT500. A person skilled in the art will know how to adjust the spindle (also referred to as cylinder or plate) and the rpm depending on the pharmaceutical solution to be analyzed. It must be considered that the final viscosity of the gel will depend on the features of the starting raw material, on its concentration and on the temperature.

In a preferred embodiment, the hyaluronic acid of the composition of the present invention is low-molecular weight, preferably very low-molecular weight, and low-viscosity hyaluronic acid. Preferably, it is sodium hyaluronate (e.g. Uromac®, Nakafarma, ES; Morales et al., The Journal of Urology 1996, 156.45-48).

In a particular embodiment, optionally combined with one or more of the features of the other embodiments of the invention, the concentration of hyaluronic acid is from 0.0001% to 0.3%, including from 0.001% to 0.1% and from 0.0001% to 0.09%, preferably 0.001%-0.012%, more preferably 0.002% to 0.008%, and even more preferably from 0.003% to 0.006%.

Water-soluble compounds derived from cellulose are well known by a person skilled in the art. They include but are not limited to methylcellulose, ethylcellulose, methylethylcellulose, ethylhydroxyethylcellulose, methylhydroxyethylcellulose, hydroxyethylcellulose, hydroxypropylcellulose, hydroxypropylmethylcellulose, carboxymethylcellulose, carboxymethylhydroxyethyl cellulose, alkyl cellulose and combinations thereof.

In a particular embodiment of the composition of the invention, optionally combined with one or more of the features of the other embodiments of the invention, the concentration of the water-soluble polymer derived from cellulose is from 0.01% to 1%, more preferably from 0.1% to 0.5%. In a more preferred embodiment, the concentration of water-soluble polymer derived from cellulose is from 0.1% to 0.4%, more preferably from about 0.2% to about 0.3%.

In another preferred embodiment, the present invention refers, optionally combined with one or more of the features of the other embodiments of the invention, to a (preferably aqueous) composition comprising:
  a water-soluble polymer derived from cellulose at a concentration from 0.005% to 0.4%; and
  hyaluronic acid at a concentration from 0.0001% to 0.09%.

Preferably, the viscosity of said composition is from 5 to 100 mPa*s, more preferably from 5 to 50 mPa*s, even more preferably from 10 to 40 mPa*s.

Said water-soluble polymer derived from cellulose (for example: carboxymethylcellulose) typically has a molecular weight of more than 500 kDa, preferably more than 800 kDa, more preferably around 900 kDa.

Carboxymethylcellulose or CMC is an organic compound derived from cellulose, made up of carboxymethyl groups bound to hydroxyl groups, present in glucopyranose polymers, and having the general formula $R_n OCH_2$—COOH. As it is used herein, the term also comprises pharmaceutically acceptable salts thereof, such as sodium or potassium salts. It is often used as sodium carboxymethylcellulose, also called carmellose sodium. Preferably, said carboxymethylcellulose is sodium carboxymethylcellulose.

In a particular embodiment of the composition of the invention, optionally combined with one or more of the features of the other embodiments of the invention, the concentration of carboxymethylcellulose is from 0.005% to 2% or from 0.005% to 1.9% or from 0.005% to 1.8% or from 0.005% to 1.7% or from 0.005% to 1.6% or from 0.005% to 1.5%. Preferably, the concentration of carboxymethylcellulose is from 0.025% to 1.5%, more preferably from 0.01% to 1%, even more preferably from 0.1% to 0.5%.

In another particular embodiment of the pharmaceutical composition of the invention, the concentration of carboxymethylcellulose is less than 2%, 1.9%, 1.8%, 1.7%, 1.6% or 1.5%, preferably less than 1%, more preferably less than 0.5%.

In a particular preferred embodiment, the concentration of carboxymethylcellulose is from about 0.3% to about 0.2%.

The carboxymethylcellulose can be high-, medium- or low-viscosity carboxymethylcellulose. Therefore, for example, the following table defines a CMC solution according to its high, medium or low viscosity, providing viscosity ranges for each of said classifications where said values have been measured in a 2% aqueous solution (for example in water or physiological saline) and at 20° C. Said conditions were those used in producing the solution of the example.

| CARBOXYMETHYLCELLULOSE Sodium Salt | VISCOSITY (2% sol. at 20° C.) |
| --- | --- |
| LOW | 25-50 cP |
| MEDIUM | 400-800 cP |
| HIGH | 1500-3500 cP |

The viscosity can be expressed in centiPoises(cP). 1 Poise=dynaxsec/cm2=1 g/cmxsec. Sometimes the viscosity is expressed in milliPascal-second (mPa·s), pressure measurement in IS. 1 Pascal=1 Newton×m$^2$; Conversion factor: (1 cP=10$^{-3}$ Pas=1 mPa·s).

In a particular embodiment, optionally combined with one or more of the features of other embodiments of the invention, the water-soluble polymer derived from cellulose (for example: carboxymethylcellulose) has a viscosity of 500 to 4.500 mPa*s, preferably from 1,000 to 3,000 mPa*s, more preferably from 1,500 to 2,500 mPa*s, even more preferably from 2,200 mPa*s to 2,300 mPa*s (for example: 2,237 mPa*s), when the viscosity ranges of said polymer derived from water-soluble cellulose (e.g. CMC) are measured in a 1% aqueous solution (for example in water or physiological saline) at 25° C., for example with a Brookfield LV viscometer using spindle 3 at 30 rpm.

The rheological properties of the mixture of CMC with sucrose (Cancela, M. A et al., 2005 "Effects of temperature and concentration on carboxymethylcellulose with sucrose rheology" Journal of Food Engineering, Vol. 71, pp 419-424) have previously been described, and it has been found that both with sucrose and without it, the mixture acts like a pseudoplastic. The variation in strain rate in response to tangential stress is exponential; and by increasing the concentrations of CMC and sucrose (glucose+fructose), the viscosity increases. The opposite happens when the temperature increases.

In a preferred embodiment, optionally combined with one or more of the features of the other embodiments of the invention, said carboxymethylcellulose is sodium carboxymethylcellulose, has a viscosity greater than 1,000 mPa*s in a 1% aqueous solution, and it is found in said composition at a concentration from 0.2% to 0.3%.

The composition (preferably pharmaceutical solution) of the invention can further comprise other polysaccharides, preferably having pseudoplastic rheological properties. Examples of polysaccharides are hydroxypropylmethylcellulose, xanthan gum, carrageenan, gellan gum, guar gum, locust bean gum, and sacran. Combinations thereof can also be used. In a particular embodiment, the composition (preferably pharmaceutical solution) of the invention comprises CMC as the only polysaccharide.

Additionally, the composition (preferably pharmaceutical solution) of the invention can contain other active ingredients and/or pharmaceutical excipients, such as an osmotic pressure regulating agent, a pH regulating agent, a preserving agent, a dyeing agent, and one or more active ingredients (for example: a vasoconstricting or hemostatic agent).

Said composition is preferably an aqueous composition. Said aqueous composition conventionally comprises water or an aqueous solution. Non-limiting examples of aqueous solutions include:

Water.
Normal saline solution (physiological saline): contains 0.9% sodium chloride or 154 mmol/L.
Hypertonic saline solution: contains from 3% to 5% sodium chloride or 513-855 mmol/L.
Hypotonic saline solution: contains 0.45% sodium chloride or 77 mmol/L.
Ringer's lactate solution: e.g.: 102 mmol/L of sodium chloride; 28 mmol/L of lactate sodium; 4 mmol/L of potassium chloride, and 1.5 mmol/L of calcium chloride.
5% dextrose solution: supplies a concentration of 278 mmol/L of glucose.
Plasma-Lyte type solution: mixture similar to lactated Ringer's, with the presence of ions magnesium, acetate and gluconate.
Hypertonic glucose serum: contains 10%, 20%, 40% glucose, with concentrations of 278×2, 278×4, 278×8 mmol/L.
Glucosaline solution: conventionally contains 0.45% chloride sodium and 5% glucose.
Albumin solution: contains between 5-25% of sterile human albumin in water for injection.

In a preferred embodiment, said aqueous solution comprises physiological saline.

In a particular embodiment, optionally combined with one or more of the features of the other embodiments of the invention, the composition (preferably pharmaceutical solution) of the invention further comprises 1-30% of an osmotic pressure and/or pH regulating agent, preferably selected from a sugar, a polyalcohol and a salt and combinations thereof. In a particular embodiment of the composition (preferably pharmaceutical solution) of the invention, said regulating agent is found at a concentration of 10%-20%, preferably 16-18%, more preferably at 17.5%.

Examples of polyalcohols include mannitol, xylitol, erythritol, threitol, ribitol, myoinisitol, galactitol, sorbitol, glycerol, derivatives and combinations thereof. Sorbitol, glycerol and combinations thereof are particularly preferred.

In a particular embodiment, said osmotic pressure and/or pH regulating agent is a sugar, preferably a monosaccharide and/or a disaccharide. The term disaccharide can include any disaccharide. Examples of disaccharides include lactose, trehalose, sucrose, maltose, isomaltose, cellobiose, isosucrose, isotrehalose, sorbose, turanose, melibiose, gentiobiose, and mixtures thereof, preferably, lactose, trehalose, sucrose, and combinations thereof. The term monosaccharide can include any monosaccharide, such as, for example, mannose, glucose (dextrose), fructose (levulose), galactose, xylose, ribose or any combination thereof. In a particular embodiment, optionally combined with one or more of the features of the other embodiments of the invention, said sugar is a monosaccharide. In a preferred embodiment, said sugar is fructose. Said sugar can be also a polysaccharide, for example inulin, which is made up of fructose units. Said sugar (e.g. fructose) can further act as a preserving agent and coadjuvant of the carboxymethylcellulose in relation to its pseudoplastic effect.

Said salt is preferably sodium chloride, although other salts such as potassium chloride, sodium citrate, magnesium sulfate, calcium chloride, sodium hypochlorite, sodium nitrate, mercury sulfide, sodium chromate and magnesium dioxide, as well as phosphate and calcium salts, can also be used. In a particular embodiment, optionally combined with one or more of the features of the other embodiments of the invention, the composition (preferably pharmaceutical solution) of the invention comprises a saline solution, preferably physiological saline (0.9% NaCl).

Preferably, said composition (preferably pharmaceutical solution) has an osmolarity of 500-3,000 mOs/L, preferably 1,500-2,500 mOs/L, more preferably 1,700 mOs/L.

Examples of pH regulating agents include Tris-HCl buffer, acetate buffer, citrate and phosphate buffer or combinations thereof. The term "acetate buffer", "citrate buffer" and "phosphate buffer" as used herein can refer to a buffer system comprising an organic acid (acetic acid, citric acid and phosphoric acid, respectively) and a salt thereof. Each of them can be added in a sufficient amount. The pH of the composition according to the present invention is in the range from 3 to 8, preferably in the range from 4 to 7, more preferably between 5 and 6.

The composition (preferably pharmaceutical solution) of the invention can further comprise a dye, which is preferably water-soluble, such as indigo carmine, methylene blue, tartrazine, erythrosine and quinoline yellow, more preferably indigo carmine or methylene blue.

Conventionally, a diluted dye is normally used. The dye colors the mucosa and makes it easier to assess the lesion depth and accurately demarcate its borders (Larghi A, Waxman I. "State of the art on endoscopic mucosal resection and endoscopic submucosal dissection", Gastrointest Endosc Clin North Am. 2007; 17:441-69).

The composition (preferably pharmaceutical solution) of the invention can further comprise one or more active ingredients. Said active ingredient can be a vasoconstricting agent for example. Epinephrine (also referred to as adrenalin) is generally used. Alternative vasoconstricting agents that can be used alone or combined with epinephrine include but are not limited to noradrenalin, caffeine, theophylline, and phenylephrine. Each of them can be added in a suitable amount to control bleeding during resection of the lesion. In a preferred embodiment, said vasoconstricting agent is epinephrine at a concentration of 0.000025-0.5%, preferably 0.00025-0.05%, more preferably 0.001-0.01%, even more preferably 0.005%.

Other active ingredients that can be used in the composition of the invention include but are not limited to inulin (anti-inflammatory/antibacterial) for example at a concentration from 0.1 to 50%; citric acid (antioxidant/coagulant/pH corrector) for example at a concentration from 0.1 to 20%; zinc (healing agent/antioxidant) for example at a concentration from 0.1 to 20%; amino acids such as glutamine, alanine and/or arginine (immunomodulatory amino acids favoring the healing process) for example at a concentration from 0.1 to 20%.

In a particular embodiment, the composition (preferably pharmaceutical solution) of the present invention is essentially free of one or more preservatives, such as benzyl alcohol, phenol, m-cresol, chlorobutanol and benzalkonium chloride. In another embodiment, a preservative can be included in the formulation, particularly when the formulation is a multi-dose formulation. The concentration of preservative can be in the range from about 0.1% to about 2%, more preferably from about 0.5% to about 1%.

In a particular preferred embodiment, the composition (preferably pharmaceutical solution) of the invention, optionally combined with one or more of the features of the other embodiments of the invention, comprises or consists of:
0.0001% to 5% hyaluronic acid (preferably, 0.0001% to 0.09%)
0.005% to 2% sodium carboxymethylcellulose (preferably, 0.005% to 0.4%)
fructose or inulin, qsf pH: 5-6
physiological saline, qsf,
optionally, 0.0001-0.01% epinephrine
optionally, a dye (0.01-0.1 ml, preferably 0.05 ml, of a 0.1 to 5% solution), where preferably said hyaluronic acid is low-molecular weight and low-viscosity hyaluronic acid and/or the carboxymethylcellulose is high-viscosity carboxymethylcellulose.

Preferably, the composition (preferably pharmaceutical solution) of the invention, optionally combined with one or more of the features of the other embodiments of the invention, comprises or consists of:
0.003% hyaluronic acid
0.2% to 0.3% sodium carboxymethylcellulose
fructose or inulin, qsf pH: 5-6
physiological saline, qsf
optionally, 0.005% epinephrine
optionally, a dye (0.01-0.1 ml, preferably 0.05 ml, of a 0.1 to 5% solution).

In other particular embodiments, the composition of the invention further comprises citric acid at a concentration from 0.5% to 3% (e.g. 1%), zinc at a concentration from 0.5% to 3% (e.g. 2%), glutamine and alanine (e.g. Dipeptiven®) at a concentration from 2% to 10% (e.g. 5%) and polyethylene glycol (e.g. PEG400) at a concentration from 0.5% to 3% (e.g. 1%).

In addition to those described in the examples, the following formulations were tested in patients, obtaining similar results:
A)
0.003% hyaluronic acid
0.2% to 0.3% sodium carboxymethylcellulose
fructose, qsf pH: 5-6
physiological saline, qsf
1% citric acid
2% zinc
5% glutamine and alanine (Dipeptiven®)
1% PEG 400
1%-0.05 mL indigo carmine
(pH: 5-6).
B)
0.003% hyaluronic acid
0.2% to 0.3% sodium carboxymethylcellulose
10% inulin
physiological saline, qsf
1% citric acid
2% zinc
5% glutamine and alanine (Dipeptiven®)
1% PEG 400
1%-0.05 mL indigo carmine
(pH: 5-6).

The composition (preferably pharmaceutical solution) of the invention is preferably a sterile composition (preferably solution). Today it is recognized that a product may be considered sterile when the probability of survival of any microorganism is less than $10^{-6}$. There are several methods that are well known by a person skilled in the art for sterilizing pharmaceutical compositions, which can be generically classified as physical and chemical sterilization methods. Among those physical agents are heat sterilization techniques, which can be dry heat or moist heat, ultraviolet or ionizing radiations, and sterilizing filtration systems. Chemical sterilization conventionally refers to the use of liquid or gaseous antiseptics (e.g. ozone). In the present invention, the sterilizing agent is preferably a physical agent.

In a particular embodiment, optionally combined with one or more of the features of the other embodiments of the invention, said composition (preferably solution) is obtained by a method comprising a sterilizing filtration step with a filter between 0.2 μm-1 μm, preferably 0.45 μm. For example, an antibacterial, pressure-resistant, 0.45 μm air filter can be used. The material of the membrane can be an acrylic copolymer on a nylon support.

In a particular embodiment, optionally combined with one or more of the features of the other embodiments of the invention, said composition/solution is obtained by a method comprising a moist heat sterilization step. Existing methodologies can be classified according to the temperature used: >100° C. (e.g. pressurized steam (autoclave); around 100° C. (flowing steam) or less than 100° C. (tyndallization). In a preferred embodiment, said moist heat sterilization method uses a temperature equal to or less than 100° C., preferably the sterilization step is by tyndallization. Not subjecting the composition of the invention to temperatures greater than 100° C. allows avoiding a loss of viscosity of the solution, since at high temperatures, heat conventionally reduces viscosity of a solution with pseudoplastic characteristics.

Method for Obtaining a Composition of the Invention

In a second aspect, the present invention relates to a method for obtaining a composition comprising the following steps:
a) mixing a gel of a water-soluble polymer derived from cellulose having a viscosity of 3,000 to 5,000 mPa*s in a 2% aqueous solution with an aqueous solvent;
b) mixing the solution obtained in step a) with hyaluronic acid; and
c) optionally, a dye and/or one or more active ingredients or excipients is incorporated during step a) or after obtaining said composition in a).

Preferably, said mixing process is carried out until obtaining a composition with a viscosity from 5 to 100 mPa*s, more preferably from 5 to 50 mPa*s, even more preferably from 10 to 40 mPa*s.

In a preferred embodiment, the concentration of said water-soluble polymer derived from cellulose in the composition according to the second aspect of the invention is from 0.005% to 2%, and the concentration of hyaluronic acid is from 0.0001% to 0.5%. Preferably, in said composition the concentration of said polymer derived from water-soluble cellulose is from 0.005% to 0.4%, and the concentration of hyaluronic acid is from 0.0001% to 0.09%.

Said mixing method in a) and b) is generally performed under constant stirring from 200 rpm to 500 rpm (preferably about 300 rpm) and at constant heat at a temperature from 45° C. to 55° C. (preferably about 50° C.).

It is also contemplated that other excipients and/or active ingredients have previously been dissolved in the aqueous solvent used in step a), as described in other aspects of the invention, preferably an osmotic pressure and/or pH regulating agent, more preferably fructose or inulin, has been dissolved.

Said gel of a water-soluble polymer derived from cellulose having a viscosity from 3,000 to 5,000 mPa*s in solution at 2% can be prepared for example by means of a method comprising:

dissolving said polymer at 2% in an aqueous solvent by maintaining constant stirring from 200 rpm to 500 rpm and constant heat at a temperature from 45° C. to 55° C. until reaching a desired viscosity from 3000 to 5000 mPa*s.

Preferably, said stirring process is carried out between 3 and 6 hours, preferably around 5 hours.

Said water-soluble polymer derived from cellulose is preferably carboxymethylcellulose. Additionally, said aqueous solvent is preferably physiological saline. Other features of the composition as well as particular and preferred embodiments thereof have been described hereinabove.

Said method of obtaining a pharmaceutical composition of the invention can further comprise a sterilization step. Possible sterilization methods have been described above.

In a particular embodiment, said sterilization step is performed by means of filtration with a filter between 0.2 μm and 1 μm, preferably 0.45 μm. In another particular embodiment, said sterilization step is performed by means of heat sterilization, preferably by tyndallization.

Said method can comprise an additional step for the aseptic filling of the vessel (for example: a syringe) containing the composition of the invention.

In a third aspect, the present invention relates to a composition obtained or obtainable by a method as described in the second aspect of the invention. Preferably, said composition is a composition according to the first aspect of the invention obtained by a method according to the second aspect.

Uses of the Composition of the Present Invention

The composition of the present invention is preferably a pharmaceutical composition. Said pharmaceutical composition is formulated to be compatible with the selected administration route. Methods for carrying out said administration are known by a person skilled in the art. They include, for example, injections by parenteral route (preferably with the exception of the intravascular route), such as by subcutaneous, intraarticular, mucosal, submucosal route. The oral, nasal, ophthalmic, rectal or topical routes are also contemplated, as are controlled-, delayed- or sustained-release formulations. In a particular embodiment, said formulation is for submucosal injection.

In another additional aspect, the invention relates to the composition of the invention for use as a medicament.

In a related aspect, the invention refers to the use of the composition (preferably pharmaceutical composition) of the invention as a carrier for the administration of compounds useful in diagnostic, surgical and/or therapeutic treatment methods. Said compounds include active ingredients with pharmacological activity as well as radioisotopes or other compounds commonly used for diagnostic purposes.

In a related aspect, the invention relates to the composition of the invention for use, preferably as a lubricant, in the treatment of syndromes or diseases affecting the joints.

Additionally, the invention relates to the composition according to the first and third aspect of the invention for use in a method of treatment requiring the separation of tissues, where said composition is administered by means of injection, preferably by means of endoscopic injection, in one of the tissues to be separated or in a tissue located between both.

In a preferred embodiment, the invention relates to a (preferably aqueous) composition comprising:

a water-soluble polymer derived from cellulose at a concentration from 0.005% to 0.4%; and
hyaluronic acid at a concentration from 0.0001% to 0.3%;

for use in a method of treatment requiring the separation of different layers of tissue, where said composition is administered by means of injection, preferably by means of endoscopic injection, in one of the tissues to be separated or in a tissue located between both.

Said aqueous composition, preferred features and particular embodiments thereof, as well as the method of obtaining same have been described in previous aspects of the invention.

In an additional aspect, the invention relates to the use of a composition (preferably pharmaceutical solution) according to the first or third aspect of the invention in the manufacturing of a medicament for the treatment of lesions in the mucosa comprising the resection of a portion of the mucosa, preferably the mucosa of the gastrointestinal tract.

In a related aspect, the invention refers to the composition (preferably pharmaceutical solution) according to the first or third aspect of the invention for use in a method for the treatment of lesions in the mucosa, wherein said method comprises the resection of a portion of the mucosa. Additionally, in another aspect the invention relates to a method for the treatment of lesions in the mucosa in a patient, wherein said method comprises the injection, which is conventionally endoscopic, of a therapeutically effective amount of said composition (preferably solution) for the resection of a portion of the mucosa.

Additionally, the invention also relates to the composition of the invention for use in the treatment of lesions in the mucosa of the gastrointestinal tract. In a related aspect, the invention relates to the use of the composition of the invention in manufacturing a medicament for the treatment of lesions in the mucosa of the gastrointestinal tract. Finally, also relates to a method for the treatment of lesions in the mucosa of the gastrointestinal tract, wherein said method comprises the injection, which is conventionally endoscopic, of a therapeutically effective amount of said composition.

Preferably said composition (preferably aqueous) comprises:

a water-soluble polymer derived from cellulose at a concentration from 0.005% to 0.4%; and
hyaluronic acid at a concentration from 0.0001% to 0.3%.

Said aqueous composition, preferred features and particular embodiments thereof, as well as the method of obtaining same have been described in previous aspects of the invention.

The invention also relates to the use of the composition (preferably pharmaceutical solution) of the invention as a composition (preferably solution) for submucosal injection or as a lifting agent in a method of treatment (for example, method of surgical treatment) of endoscopic resection.

The composition according to the present invention is particularly suitable for use in the resection of the mucosa. Said resection conventionally comprises the endoscopic resection of lesions or damaged tissue in the mucosal layer, such as neoplastic lesions (e.g. early-stage tumors) or pre-neoplastic lesions (e.g. polyps).

Several techniques for resection of the mucosa have been described. Specific examples of techniques for the endoscopic resection of the mucosa include endoscopic submucosal resection (EMR) or mucosectomy, endoscopic submucosal dissection (ESD), laparoscopic mucosal resection, uteroscopic mucosal resection, transurethral resection of a bladder tumor and laser mucosectomy. The composition according to the present invention can be used for any of these techniques for resection of the mucosa.

In a particular embodiment, said endoscopic resection is selected from the group consisting of mucosectomy and endoscopic submucosal dissection. Although not standard, mucosectomy is usually performed when the lesion is <20-30 mm, whereas endoscopic submucosal dissection is generally performed for bigger lesions (up to 6-7 cm) (B.-H. Min, et al., "Clinical outcomes of endoscopic submucosal dissection (ESD) for treating early gastric cancer: comparison with endoscopic mucosal resection after circumferential precutting (EMR-P)", Digestive and Liver Disease. 2009; 3 (41):201-9). Preferably, said endoscopic resection is an endoscopic submucosal resection (EMR) or mucosectomy.

Generally, mucosectomy comprises demarcating the area of the mucosa to be resected (the limits of the lesion), injecting a composition (preferably solution), which is preferably sterile, into the submucosa, conventionally by means of using a syringe to which an injection needle is coupled. Said composition/solution lifts the zone to be extirpated and separates it from the rest of the layers of the gastrointestinal tract so as to not causing more damage than that strictly necessary. The volume to be infiltrated is variable depending on the size of the lesion. In said intervention, a critical step is the identification of the borders of the lesion before extirpating it. Usually, >90% of lesions in mucosae are completely resected with the mucosectomy (in one or more sessions). In the meantime, endoscopic submucosal dissection consists of an "en bloc" resection of a large tumoral surface, generally colorectal. With this aim, a composition/solution which lifts the lesion is injected at the submucosal level. The mucosa adjacent to the lesion is incised with a suitable margin before the incision of the submucosal layer. To that end, complete or partial incision of the surrounding mucosa is initially performed according to the established protocol and lesion characteristics (B.-H. Min, et al., "Clinical outcomes of endoscopic submucosal dissection (ESD) for treating early gastric cancer: comparison with endoscopic mucosal resection after circumferential precutting (EMR-P)", Digestive and Liver Disease. 2009; 3 (41):201-9; Yamamoto K, et al., "Colorectal endoscopic submucosal dissection: Recent technical advances for safe and successful procedures". World J Gastrointest Endosc 2015 Oct. 10; 7 (14): 1114-1128).

The composition according to the present invention is preferably applied by means of injection into the mucosa or into the surrounding tissue, such as the submucosa, mucosa, or epithelium. Among the former, administration by means of submucosal injection is preferred.

Examples of parts of the body where the composition according to the present invention can be applied include the digestive mucosa in organs such as the esophagus, stomach, duodenum, bile duct, small intestine, large intestine, colon, rectum, and also the mucosa of respiratory organs (e.g. the lungs), or the mucosa of genitourinary organs (e.g. the urinary bladder, urethra, vagina and uterus. Among them, the mucosa of the upper digestive tract (from the esophagus to the stomach or the duodenum) and the mucosa of the lower digestive tract (the small intestine, e.g. jejunum and ileum below the duodenum), and the large intestine (colon, rectum) is preferred. Conventionally, said treatment comprises injecting the composition (preferably pharmaceutical solution) of the invention into the submucosal layer.

In a preferred embodiment, the injection site is the submucosa of an organ of the digestive tract, also herein referred to as gastrointestinal tract. The composition (preferably pharmaceutical solution) of the invention can be used combined with a direct inhibitor of smooth muscle peristalsis and locally sprayed inside the digestive tract through a spray device or forceps during endoscopy, for example, digestive tract surgery by laparotomy, endoscopic surgery, endoscopic examination of the digestive tract or another medical practice in which digestive tract peristalsis must be suppressed.

The composition (preferably solution) of the invention can be used with different apparatus for endoscopic resection. Oval-shaped multifilament polypectomy snares in variable sizes (between 30 and 10 mm) are normally used. Tables 1 and 2 of the article "Endoscopic mucosal resection and endoscopic submucosal dissection", Gastrointestinal endoscopy 2008, 68:1 11-18 describe in detail apparatus for mucosectomy (EMR) and endoscopic submucosal dissection, respectively, available on the market.

The injection of the composition (preferably pharmaceutical solution) of the invention is generally performed by means of an endoscopic injection needle.

In a preferred embodiment, optionally combined with one or more of the features described in other aspects of the invention, the composition of the invention is administered by means of endoscopic injection into the submucosal layer of an organ of the gastrointestinal tract.

The diameter of the endoscopic injection needle (G) is standard in terms of the outer diameter of the needle, and a larger gauge number means a smaller outer diameter of the needle. The gauge number of an endoscopic injection needle to be used with the pharmaceutical solution of the invention is selected depending on the surgical site, but is generally from 21 to 25G, preferably 23G. Even when they have the same gauge number, endoscopic injection needles produced by different manufacturers can have a different inner diameter. Using a needle with the smallest diameter possible is generally preferred, also being able to use needles with a size less than 25G, such as 25sG, 26, 26sG, 27G, 28G, 29G, 30G, 31G, 32G, or 33G. The size of the needle to be used will be chosen according to the viscosity characteristics of the composition and the apparatus used for administering it.

There are commercially available endoscopic injection needles designed to minimize injection pressure. In a particular embodiment, the composition (preferably pharmaceutical solution) of the invention can be injected by an operator, preferably without difficulty, even when an endoscopic injection needle having a diameter of 23G or higher is used. Generally, the effective tube length of an endoscopic injection needle is 1,000 mm or more, preferably 1,500 up to 2,500 mm.

The injection pressure of a solution for submucosal injection can be measured, for example, using a 5 or 10 ml plastic Luer-Lock syringe filled with a measurement solution. An endoscopic injection needle with a diameter of 23G and an effective tube length of 1,600 mm for the tube connected to the syringe can be used. The syringe is fixed to a texture analyzer (EZ Test 500N manufactured by Shimadzu Corporation), and the syringe piston is pushed at a constant speed of 100 mm/min. The force required to discharge the measurement solution in the syringe through the tip of the endoscopic injection needle is measured at 25° C. and is defined as the injection pressure. If the injection pressure is 14 kgf or more, the measurement solution is discharged through the tip of the endoscopic injection needle, but there are losses around the syringe piston; furthermore, the syringe piston does not move even by pushing it with one hand instead of with the texture analyzer. When the injection pressure is about 11 kgf, the measurement solution can be discharged through the tip of the needle when the syringe piston is pushed with one hand instead of with the texture analyzer. In a particular embodiment, optionally combined with one or more of the features described in other aspects of the invention, the injection pressure of the composition (preferably pharmaceutical solution) of the invention, said measurement being as described in the preceding paragraph, is preferably from 0.1 to 12 kgf, more preferably from 0.25 to 10 kgf, even more preferably from 0.5 to 10 kgf, 1.0 to 7 kgf being particularly preferred.

In another particular embodiment, optionally combined with one or more of the features described in other aspects of the invention, the retention time of the composition (preferably solution) is at least 30 minutes, preferably at least 45 minutes, for example between 30 minutes and 1 hour. More preferably, the retention time of the composition/solution is 60 minutes or more. Preferably, once the retention time ends, complete reabsorption of the solution takes place progressively. The retention time of the composition/solution is defined as the period of time in which a protuberance or bump having a sufficient height allowing the endoscope operator to distinguish the limits of the lesion and extirpate is maintained. Preferably, the mean height of the protuberance during retention time is at least 3 mm, preferably 4 mm or more, for example between 4 mm and 10 mm, between 5 mm and 8 mm or between 6 and 7 mm. Said protuberance is generally equal to 20% to 40%, preferably 30% to 35%, of the cavity of the organ in which mucosal resection is performed.

The composition according to the present invention can be loaded and stored in a container. In another aspect of the invention, a kit comprising a container containing the composition (preferably pharmaceutical solution) of the invention, and optionally, instructions for the use thereof as a composition (preferably solution) for use in a method of treatment as described in previous aspects of the invention, is further provided, preferably for use by means of submucosal injection in a method of endoscopic resection treatment.

The containers in which the pharmaceutical composition is supplied can be any conventional container which can maintain the pharmaceutical formulation of the invention, such as a syringe, preferably Luer-Lock syringes, for example between 10 to 50 ml, a vial or an ampoule. The present invention can provide an assembly comprising one or more containers containing the composition of the invention and an endoscopic injection needle. Alternatively, said kit can contain one or more endoscopic injection needles pre-loaded with the composition of the invention.

It is contemplated that any embodiment analyzed in the present specification can be implemented with respect to any composition, pharmaceutical composition, kit, medical use, method of treatment, and/or method of manufacturing a medicament of the invention, and vice versa. It will be understood that the particular embodiments described herein are shown by way of non-limiting illustrations of the invention. The main characteristic features of the present invention can be used in several embodiments without departing from the scope of the invention. Those skilled in the art will recognize, or will be capable of determining, through simple routine experimentation, a number of equivalents to the specific methods described herein. It is considered that these equivalents are within the scope of the present invention and are contemplated by the claims.

All patent publications and applications are incorporated herein by reference to the same extent as if each individual patent publication or application was specifically and individually indicated to be incorporated by reference.

The use of the word "a" may mean "one", but it is also consistent with the meaning of "one or more", "at least one" and "one or more than one". The use of the term "another"/"other" can also refer to one or more. The use of the term "or" in the claims is used to say "and/or" unless it is explicitly indicated that it only refers to alternatives or that the alternatives are mutually exclusive.

As used in this specification and claims, the words "comprise" (and any form of the word comprise, such as "comprise" and "comprises"), "have" (and any form of the word, such as "have" and "has"), "include" (and any form of include, such as "includes" and "include") or "contain" (and any form of contain, such as "contains" and "contain"), are inclusive or open and do not exclude additional elements or steps of the method that are not mentioned. As it is used herein, the expression "essentially consisting of" limits the scope of a claim to the specified materials or steps and to those not physically affecting basic and novel feature(s) of the claimed invention. As it is used herein, the expression "consisting of" excludes any element, step or ingredient not specified in the claim with the exception of, for example, impurities normally associated with the element or limitation.

As it is used herein, the term "or combinations thereof" refers to all permutations and combinations of the listed points preceding the term. For example, "A, B, C or combinations thereof" intends to include at least one of: A, B, C, AB, AC, BC or ABC, and if the order is important in a particular context, also BA, CA, CB, CBA, BCA, ACB, BAC or CAB. Continuing with this example, combinations containing repetitions of one or more points or terms, such as BBB, AAA, AB, BBC, AAABCCCC, CBBAAA, CABABB, and so on and so forth, are expressly included. The person skilled in the art will understand that conventionally there is no limit on the number of points or terms in any combination, unless it is otherwise obvious from the context.

As it is used herein, words of approximation such as, without limitation, "on", "around", "about" refer to a condition which, when so modified, is understood to be not necessarily absolute or perfect, but rather it would be considered to be close enough for the those skilled in the art to assure the designation of the condition as present. The degree to which the description can vary will largely depend on a change being able to be instituted and a person skilled in the still recognizing that the modified characteristic feature still has the required features and capabilities of the unmodified characteristic feature. Generally, but subject to prior analysis, a numerical value herein modified by a word of approximation such as "about" can vary from the established value by ±1, 2, 3, 4, 5, 6, 7, 10, 12 or 15%. Preferably said variation is 0%.

EXAMPLES

Example 1

Efficacy and Safety Study: Comparison With 10% Glycerol

Material and Methods

Retrospective study with 20 patients who went to the endoscopy practice at Hospital de Poniente, in El Ejido (Almeria) to perform endoscopic submucosal mucosectomy. A 10% glycerol solution, 5% fructose, 0.005% adrenalin solution with methylene blue was used in 10 patients. The new solution under study was used in 10 other patients: extemporaneous solution of low-density hyaluronic acid (HA) (UROMAC®) at 0.003%, sodium carboxymethylcellulose (CMC) 1500-4500 (94224, Guimana) at 0.2% characterized by a viscosity of 1,500-2,500 mPa*S in 1% dilution, fructose, qsf pH=5-6, 0.005% adrenalin, 1 drop (0.05 ml) of methylene blue in physiological saline, qsf 50 mL. The solution was packaged in BD Plastipak™ 50 mL Luer-Lock syringes and conserved between 2-8° C. until use.

Collected data: number of lesions and size (cm), number of resections for complete removal of the lesion (sessions), number of injections of the solution, volume injected into each lesion (mL), duration of the bump useful during mucosectomy (minutes), time (minutes) from the start of the endoscopic intervention until the start of reabsorption is observed, tissue vascularization (Good/Fair/Bad), generation of fumes making visibility difficult during the surgical intervention (YES/NO), bleeding during the surgical intervention (YES/NO), type of bleeding (LIGHT/MODERATE/MASSIVE), complications of the surgical intervention, progression of the tissue (in check-ups) after the administration of the drug (inflammation tissue damage).

Both solutions were produced in sterile conditions in a horizontal laminar flow hood and was filtered within the horizontal laminar flow hood with a Mini Spike Plus V® sterilizing filter (Braun). The following physicochemical stability conditions were considered: pH=5-6, visual absence of solute precipitation, as well as visual absence of particles for 30 days in both solutions. To determine microbiological stability, samples of both solutions were cultured on days 0, 7, 15, 30 after production thereof. Likewise, given the momentary impossibility to determine the viscosity, the inventors opted for determining the osmolarity of both solutions.

The solution was administered with B/BRAUN Omnifix® 10 mL Luer-Lock syringes, which were coupled to a catheter measuring 200 to 240 cm in length with a 23-gauge endoscopic injection needle. The minimum working channel required for this material measures 2.0-2.8 mm (Interject™ Contrast—Injection Therapy Needle Catheter—Boston Scientific).

Results

In all patients, the borders of the polyps were perfectly demarcated before extirpation, using diluted methylene blue. The dye stained the submucosa and allowed the perfect assessment of the depth of the eschar in the patients, and it accurately demarcated the borders. The snares used were oval-shaped multifilament snares with sizes of 30 and 10 mm, dealing with large lesions using endoscopic piecemeal resection. Monopolar current was used with a coagulation mixture according to the recommendations of the manufacturer of the electrosurgical unit.

All patients presented between 3-6 lesions, with a surface between 15-40 mm of surface area and an extirpated tissue depth between 0.5-1 mm. No difference was observed in the number of sessions for removing the lesions according to the use of one solution or another. With the 10% glycerol solution, the patients required between 100-200 mL of solution and the solution had to be reinjected in 6 patients. However, with the solution under study an average of 50 mL of solution was required and did not have to be reinjected in any patient.

After the mucosectomies, a "bump" could be observed when the solution was introduced in the intestinal submucosa, and it separated the zone of the polyps from the zone irrigated by blood vessels and muscles for the 30-45 minutes the interventions lasted, compared to the 15 minutes observed with 10% glycerol, which at times required being reinjected in patients. The use of the new formula for mucosectomy provided optimal lift of the lesion for a prolonged time, conferring greater safety.

All the patients are in clinical follow-up without presenting any complication associated with the intervention. By introducing adrenalin, the potential risk of hemorrhages was reduced and recovery was expected to be faster. Subsequently, the solution injected into the submucosa was reabsorbed without any problems and no signs of inflammation or tissue damage secondary to the solution used were observed. However, patients are still in follow-up and this must be confirmed in future visits. No massive bleeding was observed in any of the patients nor were any complications observed during the intervention.

The vascularization of the tissue subjected to surgical intervention was good. In 3 patients the moderate presence of fumes was observed with the 10% glycerol solution, which made visibility of the zone to be extirpated partially difficult, while this was not observed with the new solution.

Both solutions presented microbiological stability for at least 30 days. The mean osmolarity of the solution under study was 1.710 mOs/L, while the mean osmolarity of the 10% glycerol solution was 809 mOs/L. However, from the physicochemical viewpoint, and given the absence of studies, only a stability of 24 hours between 2-8° C. in both solutions could be recommended.

Discussion

After the mucosectomies, the result of the new formula, which has a mechanical-pharmacological effect, was shown to be optimized in our patients. A "bump" is produced when the solution is incorporated in the intestinal submucosa, and it separates the zone of the lesion from the zone irrigated by blood vessels and muscles for about 45 minutes. Therefore, when the polyp is extirpated, the risk of hemorrhages and lesions is reduced and recovery is faster. Subsequently, this solution injected into the submucosa seems to be reabsorbed without producing adverse effects, giving sufficient time to perform the mucosectomy.

The formula could have an enormous potential of use for injection in the submucosa, such as in mucosectomy of early neoplastic lesions of the digestive tract and in the submucosal endoscopic dissection. The "bump" that was generated seems to last longer with this preparation than with glycerol, physiological saline, or other products separately.

Conclusions

The advantages of this solution are a high permanence of the compound at the intestinal level, large expansion of the tissue injecting a smaller amount of product, optimal viscosity, total subsequent reabsorption of the administered product, physicochemical and microbiological stability, and all this at a very low cost.

Example 2

Efficacy and Safety Study: Retrospective Study of the Composition of the Invention in 10 Additional Patients Material and Methods Retrospective study in 10 patients who went to the endoscopy practice at Hospital de Poniente, in El Ejido (Almeria) to perform colonic endoscopic mucosal resection of flat lesions 15 mm. Solution under study: hyaluronic acid (HA) 150-250 centiPoises (UROMAC®) at 0.003%, sodium carboxymethylcellulose (CMC) 1500-4500 (94224, Guinama) at 0.2%, characterized by a viscosity of 1,500-2,500 mPa*s, fructose, qsf pH=5-6 and 0.05 mL of methylene blue in physiological saline, qsf 50 mL. To produce the mucosectomy solution, a concentration of CMC of 0.2% in the final solution is used, starting from a 2%-4.500 mPa·s stock solution. In the process of producing the 2% high-viscosity carboxymethylcellulose (CMC) ((4.474 mPa·s in 2% solution) in 0.9% saline solution, stirring was controlled at all times (gentle, with a magnetic stirrer, and the temperature of 50° C. at all times) until a gel with the desired viscosity was obtained after about 5 hours of stirring.

The following protocol was used for producing the solution under study:

35 g of fructose are weighed in a beaker and diluted with 100 mL of physiological saline, stirring until dissolution. 20 g of 2% high-viscosity carboxymethylcellulose are weighed and added to the previous solution. We maintain continuous stirring while adding 1 mL of 1% adrenalin, 6 mL of low-viscosity hyaluronic acid and 1 drop of methylene blue. It is made up to 200 mL with PS. It is stirred until complete homogenization.

Sterility is achieved by means of sterilizing filtration in a class 100 horizontal laminar flow hood (HLFH), located in a space (room) with partially controlled conditions (Class 100.000). It is taken to an HLFH and the content of the beaker is poured with a cut transfer device and 0.22 micron filter into BD Plastipak™ 50 mL Luer-Lock syringes and conserved between 2-8° C. until use.

The interventions were performed on all the patients after deep sedation, done by an anesthesiologist, with midazolam and pethidine IV. The borders of the polyps were perfectly demarcated in the patients before extirpation using diluted methylene blue. The dye stained the mucosa and allowed the perfect assessment of the depth of the eschar in the patients, and it accurately demarcated the borders. The snares used were oval-shaped multifilament snares with sizes of 30 and 10 mm, dealing with large lesions using endoscopic piecemeal resection. Monopolar current was used with a coagulation mixture according to the recommendations of the manufacturer of the electrosurgical unit.

Collected data: demographics, number of lesions, number of injections of the solution, volume injected (mL), duration of the bump useful during mucosectomy (minutes), time (minutes) from the start of the endoscopic intervention until the start of reabsorption is observed, bleeding during the surgical intervention, type of bleeding), complications of the surgical intervention, progression of the tissue (in check-ups at months 1, 3) after the administration of the drug (inflammation/tissue damage).

The solution under study was produced in sterile conditions in a horizontal laminar flow hood and was filtered within the horizontal laminar flow hood with a Mini Spike Plus V® sterilizing filter (Braun).

The solution was administered with B/BRAUN Omnifix® 10 mL Luer-Lock syringes, which were coupled to a catheter measuring 200 to 240 cm in length with a 23-gauge endoscopic injection needle. The minimum working channel required for this material measures 2.0-2.8 mm (Interject™ Contrast—Injection Therapy Needle Catheter—Boston Scientific).

Results 10 patients of the study (90% males 63.5 years of age) presented an average of 3 colonic lesions (range: 1-5), with a mean size of 27 mm (range: 15-50 mm) requiring a total of 24 mL of mucosectomy solution per patient. The solution did not have to be reinjected in any patient due to loss of consistency of the "bump". The solution remained in the intestinal submucosa for an average of 72 minutes. After the mucosectomies, several cases were observed in which the intervention lasted up to 90 minutes (3 patients) and in which the "bump" generated for separating the mucosal layer from the muscularis propia was effective throughout the entire intervention, no complications being observed in any patient during the intervention. Subsequently, the solution injected into the submucosa was reabsorbed, in all cases, without any problems and no signs of inflammation or tissue damage secondary to the solution used were observed, neither during the intervention nor during the follow-up visits in months 1 and 3 after performing the mucosectomy.

Discussion

The use of the new formula for mucosectomy provided optimal lift of large-sized colonic lesions for more than 60 minutes, conferring greater safety to the intervention. All the patients are currently in clinical follow-up without presenting any additional complication secondary to the intervention.

In this study it was observed that a "bump", which was consistent over time, was produced when the solution was introduced in the intestinal submucosa, and it separated the zone of the lesion from the zone irrigated by blood vessels and muscles for up to 90 minutes. Therefore, when the polyp is extirpated, the potential risk of complications is reduced. This prolonged permanence of the solution in the intestinal submucosa is primarily due to the mixture of two mucopolysaccharide substances.

Viscosity and osmolarity are key for the efficacy and safety of the solution, as demonstrated in the study herein presented. In this study, the solution was completely reabsorbed without generating safety problems. It is precisely here where part of the innovation lies, i.e., in using a very high-viscosity CMC, which surprisingly allowed that, in association with HA, low concentrations of both components are required to achieve an optimal clinical result in terms of efficacy and safety. Low-viscosity HA was used in the present study, but it is also possible to use medium-/high-viscosity HA.

Conclusions

In this study, it is demonstrated that the pharmaceutical composition of the invention, used in the colonic endoscopic mucosal resection in large-sized lesions, remains in the intestinal submucosa for more than 60 minutes, in some cases up to 90 minutes. This fact in all cases allowed for a safe and effective intervention in the extirpation of large-sized intestinal polyps due to the longer permanence of the compound at the intestinal level with respect to standard treatments, using a smaller amount of product.

Example 3

Characterization and Study of Stability of the Solution of the Invention: Comparison with 10% Glycerol Solution and 0.2% Hyaluronic Acid Solution Material and Methods The study was performed by the UGC de Farmacia (Pharmacy Service) of Hospital de Poniente and the Departamento de Galénica y Tecnologia Farmaceutica (Pharmaceutical Technology and Galenic Department) of the School of Pharmacy, University of Granada, in 2016. The method of producing the formulations indicated below is as described in Example 2.

Composition of the Formulations

1. A freshly prepared sample (15/02/16—Batch: M1502) with 10% glycerol+fructose, qsf pH=5-6+0.05 mL of 1% methylene blue+physiological saline, qsf 50 mL. Stored from the beginning at room temperature (Formulation 1).

2. A freshly prepared sample (15/02/16—Batch: M1502) with 0.4% hyaluronic acid+fructose qsf, pH=5-6+0.05 mL of 1% methylene blue+physiological saline, qsf 50 mL. Stored from the beginning at room temperature (Formulation 2).

3. Two freshly prepared samples (15/02/16—Batch: M1502) of the solution under study WITHOUT adrenalin (0.2% carboxymethylcellulose+0.003% hyaluronic acid+fructose, qsf pH=5-6+0.05 mL of 1% methylene blue+physiological saline, qsf 50 mL). Stored from the beginning in a refrigerator (2°-8° C.) (Formulation 3), and at room temperature (Formulation 4).

4. Two freshly prepared samples (15/02/16—Batch: M1502) of the solution under study with adrenalin (0.2% carboxymethylcellulose+0.003% hyaluronic acid+fructose, qsf pH=5-6+0.05 mL of 1% methylene blue+physiological saline, qsf 50 mL)→Stored from the beginning in a refrigerator (2°-8° C.) (Formulation 5), and at room temperature (Formulation 6).

Study of the pH

The pH of the prepared formulations was determined with a Orison micropH 200, Model 2000 pH-meter.

The pH was determined at different times. A significant variation in pH with respect to a value suitable for mucosectomy gels could indicate degradation of the solution or an erroneous production.

Rheological Study

The rheological characterization of the formulations was performed at 25° C. using a HAAKE Rheostress 1 rotational rheometer (Thermo Fisher Scientific, Karlsruhe, Germany) with a configuration having a parallel plate geometry, with a fixed lower plate and mobile upper plate (Haake PP60 Ti, 6 cm in diameter). Different spaces between plates were tested until selecting a separation of 0.1 mm.

The device consists of the following elements: Haake VT500 Viscometer and thermostatic bath with a water recirculation system (Haake C25P). The rheometer is connected to a computer provided with HAAKE RheoWin® Job Manager V. 3.3 software for carrying out the test and RheoWin® Data Manager V 3.3 software (Thermo Electron Corporation, Karlsruhe, Germany) for carrying out the analysis on the obtained data.

The viscosity and flow curves were recorded for 3 minutes during the period of acceleration or ascent of 0 at 100 $s^{-1}$, 1 minute at 100 $s^{-1}$ (period of constant velocity), and finally 3 minutes during the period of descent of 100 at 0 $s^{-1}$. The viscosity values at 100 $s^{-1}$ were determined at $t_0$ and $t_{180}$ days for the samples stored at 4 and 25° C. in triplicate.

Optical Characterization by Means of Multiple Light Scattering

For the purpose of predicting long-term stability, the formulations were evaluated by means of multiple light scattering, using the Turbiscan® Lab device (Formulaction Co., L'Union, France). The light source is a pulsed near infrared ($\lambda$=880 nm). The non-diluted samples are placed and kept in a cylindrical glass cell that is scanned in its entirety by a reading head. A light flow pattern according to the height of the sample, corresponding to the macroscopic fingerprint of the sample at a given time, is thereby obtained. The measurements were taken in triplicate and at room temperature.

Stability Study

The stability study was performed in parallel with the characterization study, for the purpose of analyzing the variations in pH, viscosity, rheological behavior and appearance, because they may be related to structural changes that may arise in the formulations.

Each magistral formula was prepared in a sufficient amount and stored in aliquots in amber vials at different temperatures: 4° C. and 25° C.

The complete characterization of each formula will be performed 24 h after production, this being day 0. The study period was 6 months.

The number of determinations performed per formula, time and temperature were 3.

The mean values and standard deviation were calculated for each of the assays. All the results were subjected to statistical ANOVA treatment for a confidence level of 95%, for the purpose of verifying if there were significant differences between the compared means.

Results and Discussion

Study of pH

The data shown below correspond to formulations 3 to 6. The measurements were taken 6 months after producing the formulations.

Formulation 3: WITHOUT adrenalin in refrigerator 5.29.
Formulation 4: WITHOUT adrenalin room temperature 5.99.
Formulation 5: WITH adrenalin in refrigerator 5.84.
Formulation 6: WITH adrenalin room temperature 5.02.

The obtained results show a slightly acidic pH. The pH values in all the formulations are between 5-6. This interval corresponds to the production pH. No significant variations are observed in the pH value based on the composition or time elapsing in the study. This fact will have an effect on the rheological stability of the formulations given that an increase in pH would increase the viscosity of systems with sodium carboxymethylcellulose (Voigt and Bornschein, 1982).

Rheological Study

Table 1 shows the mean viscosity values (mPa·s) of the samples at 100 s$^{-1}$, at time 0 and after 6 months.

TABLE 1

Viscosity values according to time (mean ± standard deviation), n = 3.

| CODE | DESCRIPTION OF THE SAMPLE | ISOLATED VISCOSITY mPa · s | |
|---|---|---|---|
| | | 0 days | 6 months |
| Formulation 1 | M1502 10% glycerol in refrigerator | 2.068 ± 4.101*10$^{-2}$<br>2.144 ± 4.105*10$^{-2}$ | 2.084 ± 4.894*10$^{-2}$<br>2.133 ± 4.894*10$^{-2}$ |
| Formulation 2 | M1502 0.2% hyaluronic acid in refrigerator | 2.056 ± 5.145*10$^{-2}$<br>2.083 ± 4.907*10$^{-2}$ | 2.244 ± 1.529*10$^{-2}$<br>2.253 ± 1.520*10$^{-2}$ |
| Formulation 3 | M1502 WITHOUT adrenaline in refrigerator | 21.56 ± 2.853*10$^{-2}$<br>20.98 ± 5.983*10$^{-2}$ | 23.84 ± 2.671*10$^{-2}$<br>23.84 ± 2.671*10$^{-2}$ |
| Formulation 4 | M1502 WITHOUT adrenaline room temperature | 13.25 ± 4.462*10$^{-2}$<br>13.25 ± 4.354*10$^{-2}$ | 8.943 ± 2.225*10$^{-2}$<br>9.611 ± 1.996*10$^{-2}$ |
| Formulation 5 | M1502 WITH adrenaline in refrigerator | 20.43 ± 2.814*10$^{-2}$<br>20.93 ± 3.850*10$^{-2}$ | 23.22 ± 2.497*10$^{-2}$<br>23.67 ± 2.343*10$^{-2}$ |
| Formulation 6 | M1502 WITH adrenaline room temperature | 13.14 ± 3.433*10$^{-2}$<br>13.19 ± 3.292*10$^{-2}$ | 12.60 ± 3.638*10$^{-2}$<br>12.55 ± 4.983*10$^{-2}$ |

The samples combining carboxymethylcellulose with hyaluronic acid have a much higher viscosity (about ten times higher) than the rest (samples with glycerol or samples with hyaluronic acid). This is due to the viscous synergism stemming from the interaction between the components of a system, such that the viscosity of the latter is greater than the sum of viscosities of the components separately.

The presence of adrenalin does not significantly affect the viscosity value.

Conserving the samples at low temperatures in a refrigerator shows a considerable increase in the viscosity value with respect to the samples conserved at room temperature. That is due to the fact that as the temperature increases, viscous forces are overcome by kinetic energy, leading to a decrease in viscosity (Cancela et al., 2005: "Effects of temperature and concentration on carboxymethylcellulose with sucrose rheology" Journal of Food Engineering, Vol. 71, pp 419-424).

These results should be taken into account for conserving the samples in the case of not achieving the efficacy required for performing the mucosectomy with the viscosity of the samples maintained at room temperature.

As regards the influence of the conservation time, no significant changes were observed, being able to consider all the stable samples during 6 months of study.

In addition to the temperature, viscosity can be greatly affected by variables such as the strain rate gradient and pressure, among others, these being the most important.

The variation the samples undergo with the rate gradient allows classifying the different types of fluids that can be found from the rheological viewpoint.

Therefore, the rheological characterization served not only to evaluate the stability of the formulations but also to learn about the flow behavior of the final system.

The behavior of the formulations is one of the essential criteria in the development of medical devices, because it intervenes in the functional properties of the final product during administration (mechanical behavior), quality control, the design of basic operations such as pumping, mixing, packaging, storage and physical stability.

Figure 2:
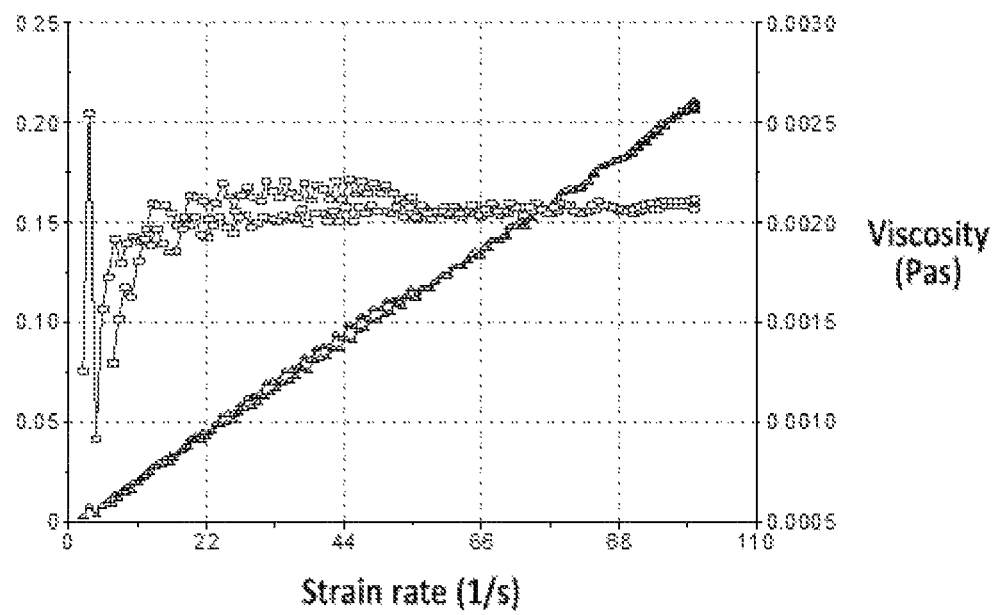
FIG. 2 shows a viscosity curve (squares) and flow curve (triangles) of Formulation 1—Sample M1502 Glycerol at time 6 months (replicate 1).
Figure 3:
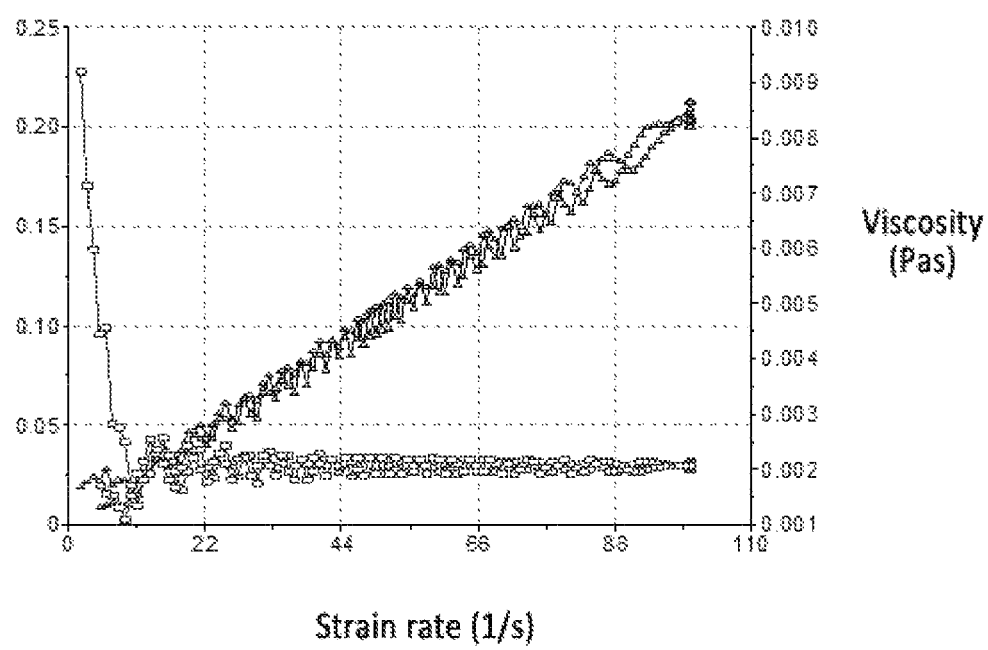
FIG. 3 shows a viscosity curve (squares) and flow curve (triangles) of Formulation 2—Sample M1502 Hyaluronic acid at time 0 (replicate 1).
Figure 4:
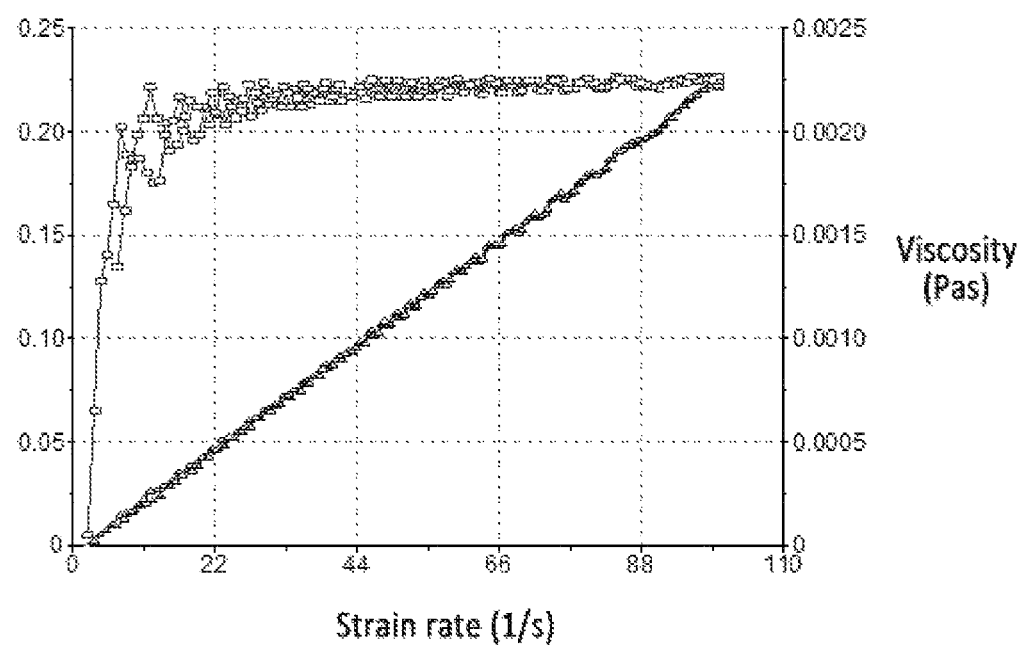
FIG. 4 shows a viscosity curve (squares) and flow curve (triangles) of Formulation 2—Sample M1502 Hyaluronic acid at time 6 months (replicate 1).
Figure 5:
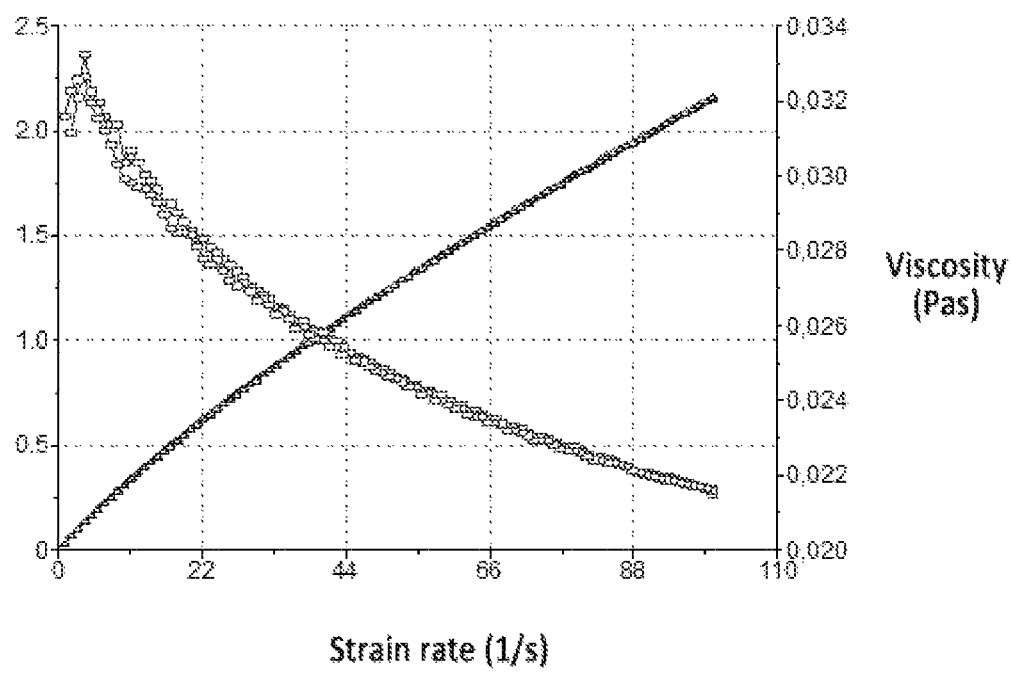
FIG. 5 shows a viscosity curve (squares) and flow curve (triangles) of Formulation 3—Sample M1502 without Adrenalin—refrigerator, at time 0 (replicate 1).
Figure 6:
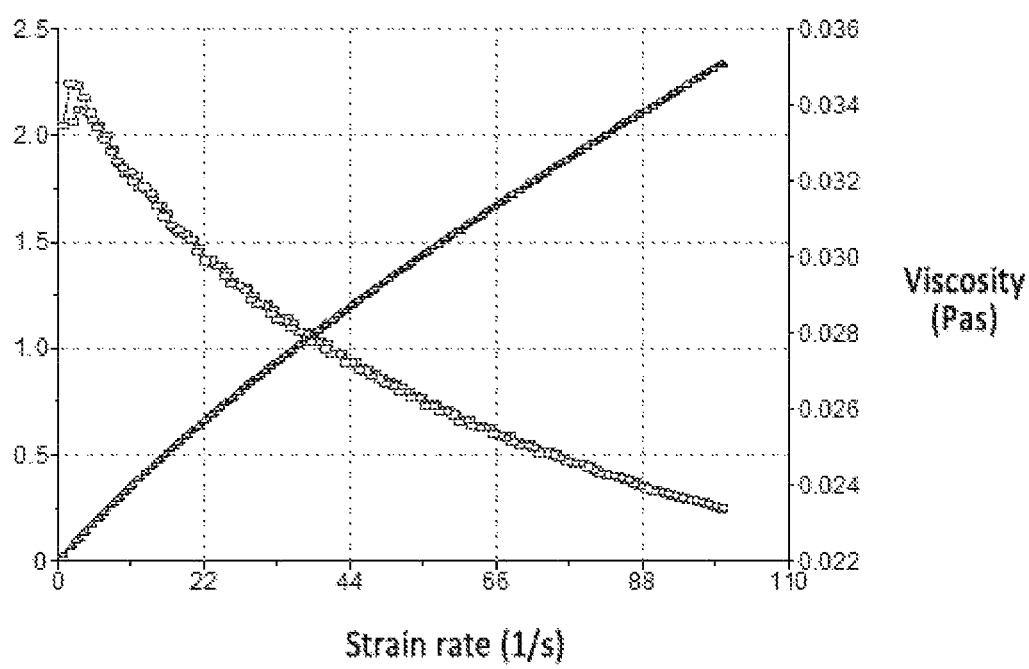
FIG. 6 shows a viscosity curve (squares) and flow curve (triangles) of Formulation 3—Sample M1502 without Adrenalin—refrigerator, at time 6 months (replicate 2).
Figure 7:
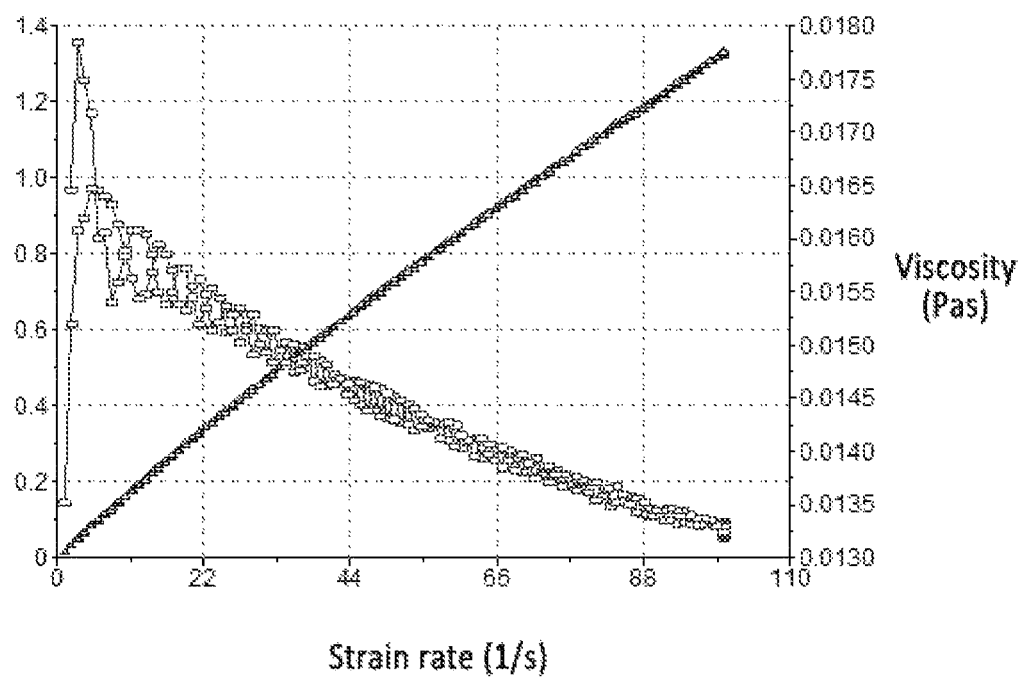
FIG. 7 shows a viscosity curve (squares) and flow curve (triangles) of Formulation 4—Sample M1502 without Adrenalin—room temperature, at time 0, (replicate 2).
Figure 8:
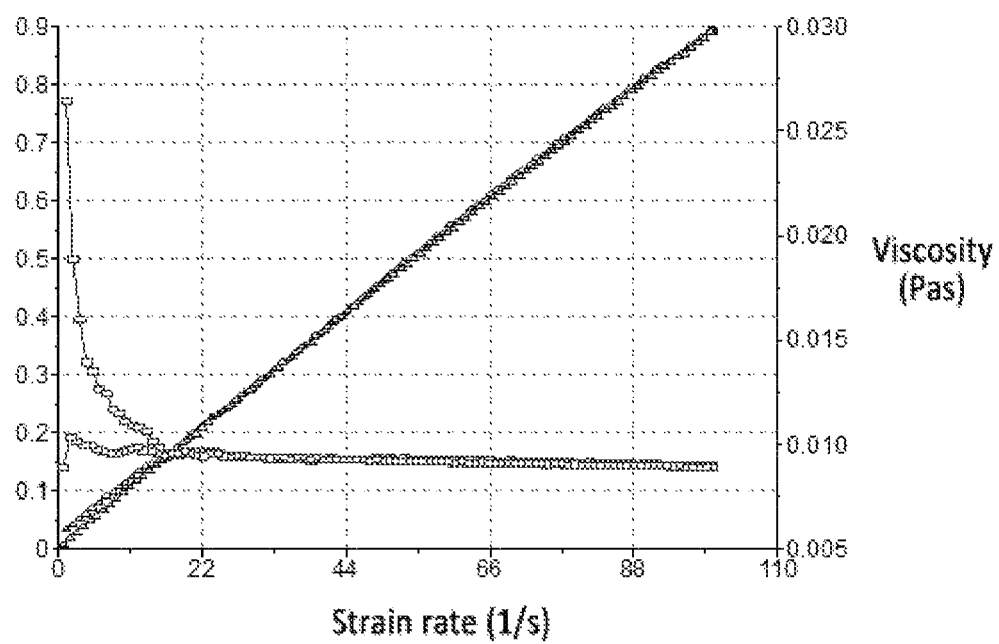
FIG. 8 shows a viscosity curve (squares) and flow curve (triangles) of Formulation 4—Sample M1502 without Adrenalin—room temperature, at time 6 months (replicate 1).
Figure 9:
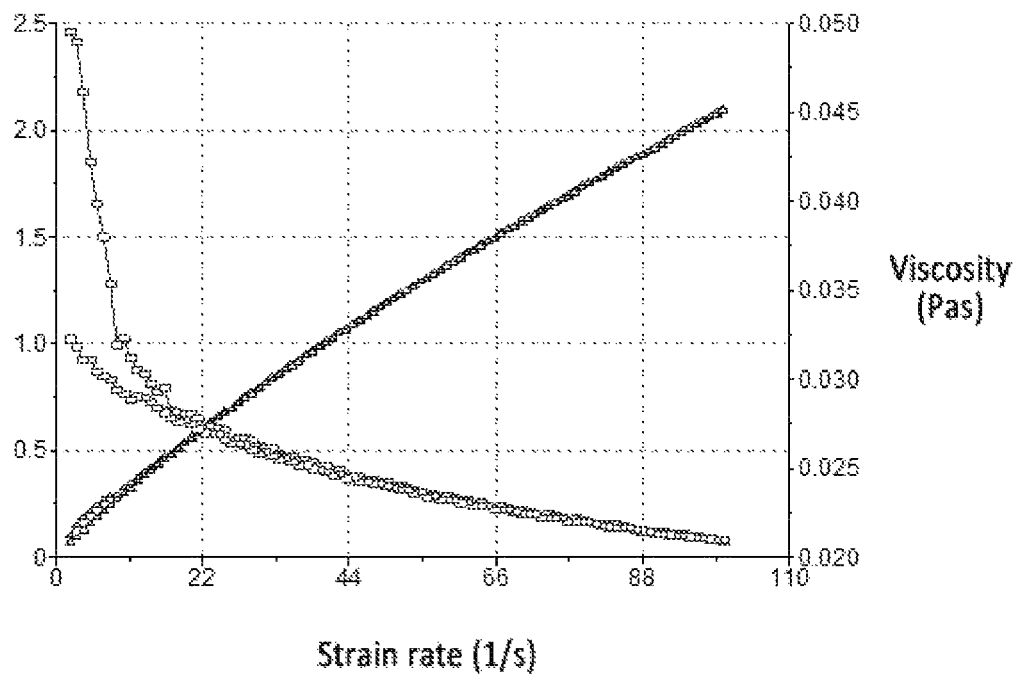
FIG. 9 shows a viscosity curve (squares) and flow curve (triangles) of Formulation 5—Sample M1502 with Adrenalin—refrigerator, at time 0 (replicate 2).
Figure 10:
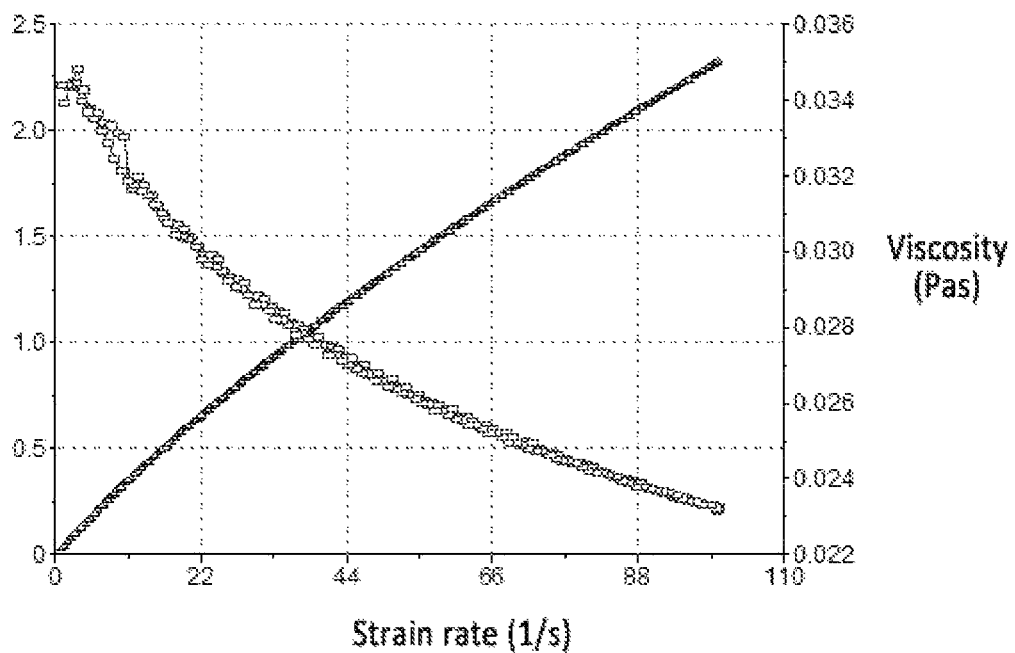
FIG. 10 shows a viscosity curve (squares) and flow curve (triangles) of Formulation 5—Sample M1502 with Adrenalin—refrigerator, at time 6 months (replicate 1).
Figure 11:
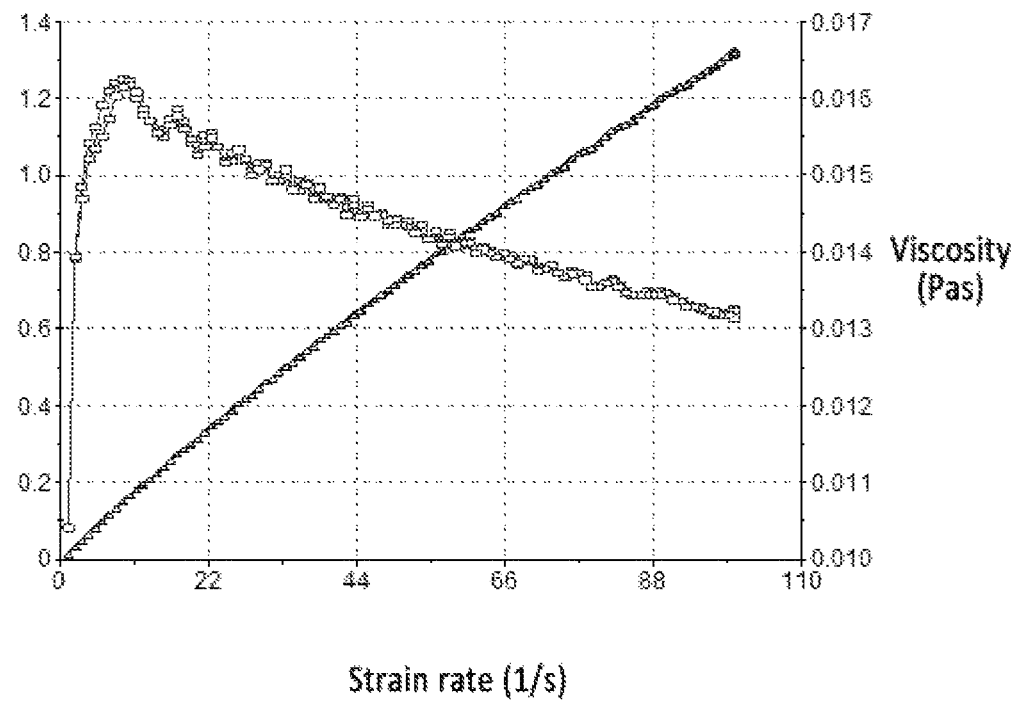
FIG. 11 shows a viscosity curve (squares) and flow curve (triangles) of Formulation 6—Sample M1502 with Adrenalin—room temperature, at time 0 (replicate 2).
Figure 12:
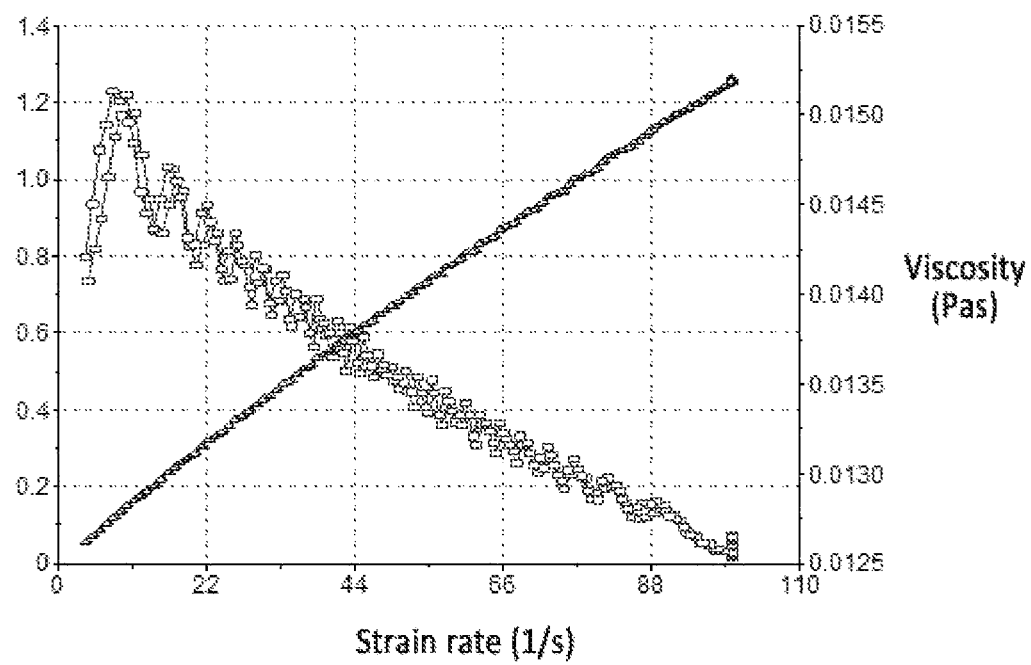
FIG. 12 shows a viscosity curve (squares) and flow curve (triangles) of Formulation 6—Sample M1502 with Adrenalin—room temperature, at time 6 months (replicate 1).

FIGS. 1 to 12 show the viscosity curve (squares) and flow curve (triangles) of the studied mucosectomy formulations. Shear stress versus strain rate ($\tau$ vs. D) is represented in the flow curve, whereas viscosity according to strain rate ($\mu$ vs. D) is depicted in the viscosity curve.

As can be seen, formulation 1 (at 6 months) and formulation 2 (at time 0 and 6 months) have Newtonian behavior, the flow curve is a straight line starting at the origin, i.e., there is a linear relationship between shear stress and strain rate. Furthermore, it is seen in the viscosity curve that viscosity is constant for any strain rate applied. This behavior continues to be maintained over the time of study, i.e., 6 months, in the formulation produced with hyaluronic acid.

However, in the case of the formulation based on glycerol this behavior varies over time, showing a plastic flow at time 0. According to the drawing, this type of fluid behaves like a solid until it exceeds a minimum shear stress (threshold stress) and after said value, it behaves like a liquid. Nevertheless, it can be seen how a virtually constant apparent viscosity value is reached at intermediate strain rates (50 s$^{-1}$), which implies a Newtonian behavior.

As regards the formulation of the invention, the viscosity tends to decrease as the shear rate increases. This behavior is typical of pseudoplastic fluids. In this case, the formulations produced with carboxymethylcellulose combined with hyaluronic acid have a high viscosity at rest that can reach values close to 35 or 16 mPa·s, at 4° C. and 25° C., respectively. This is ideal from the technological viewpoint if sedimentation is to be prevented since it would complicate aggregation of the particles of other active ingredients and/or pharmaceutical excipients such as an osmotic pressure regulating agent, pH regulating agent, a dyeing agent, and a vasoconstricting or hemostatic agent. It is also ideal from the physiological viewpoint, as the high viscosity will provide a bump or protuberance suitable for precisely removing the lesion. This behavior is similar, regardless of the conservation temperature or the presence of adrenalin.

Thixotropy is a property associated with the construction and rupture of structures under stress. Thixotropic fluids are characterized by a change in their internal structure by applying stress. A rupture of intramolecular chains occurs, the viscosity gradually decreases when a force is applied, and after a standstill time it increases again, as said force ceases due to the reconstruction of its structures; this means that they exhibit a viscosity—time relationship. The area of the hysteresis cycle can be considered an estimate of the degree of thixotropy, and it is generally admitted that a larger area of the hysteresis cycle will have stronger thixotropic properties and therefore a slower structural recovery.

The thixotropy values of the tested samples are included in Table 2:

TABLE 2

Thixotropy values of the tested formulations

| CODE | DESCRIPTION OF THE SAMPLE | Thixotropy |
|---|---|---|
| 3 | M1502 WITHOUT adrenalin in refrigerator 0 days 6 months | 0.9597 Pa/s, A(1) = 119.2 Pa/s, A(2) = 0.2791 Pa/s, A(3) = 118.5 Pa/s 0.9066 Pa/s, A(1) = 128.4 Pa/s, A(2) = 0.2875 Pa/s, A(3) = 127.7 Pa/s |
| 4 | M1502 WITHOUT adrenalin room temperature 0 days 6 months | 0.2927 Pa/s, A(1) = 70.17 Pa/s, A(2) = 0.2973 Pa/s, A(3) = 70.17 Pa/s 0.9064 Pa/s, A(1) = 46.28 Pa/s, A(2) = 0.0652 Pa/s, A(3) = 45.44 Pa/s |
| 5 | M1502 WITH adrenalin in refrigerator 0 days 6 months | 1.621 Pa/s, A(1) = 116.2 Pa/s, A(2) = 0.3593 Pa/s, A(3) = 115 Pa/s 1.334 Pa/s, A(1) = 127.9 Pa/s, A(2) = 0.2593 Pa/s, A(3) = 126.9 Pa/s |
| 6 | M1502 WITH adrenalin room temperature 0 days 6 months | 0.3441 Pa/s, A(1) = 69.99 Pa/s, A(2) = 0.2137 Pa/s, A(3) = 69.86 Pa/s 0.235 Pa/s, A(1) = 65.9 Pa/s, A(2) = 0.236 Pa/s, A(3) = 65.9 Pa/s |

The studied samples showed virtually negligible thixotropy values, and therefore are fluids that are virtually independent on the application time. This rather insignificant dependence of the viscosity on time is due to the fact that the formulations with sodium carboxymethylcellulose (CMC-Na) and hyaluronic acid have a rigid enough structure to remain unchanged with shear, with insignificant structural breakdown. This behavior is maintained 6 months after production.

There are many models that have tried to explain the behavior of non-Newtonion fluids. In this work, the obtained data were assigned to the following: Newton, Bingham, Ostwald-de-Waele, Herschel-Bulkley and Casson. Tables 3 and 4 show the best model for each formulation and the values of each parameter, respectively. The criterion for selecting the best model was based on the fit with the highest linear correlation coefficient (r). For formulations 1 and 2, it was necessary to furthermore take into account the Chi-square value.

Based on the results obtained for the formulations with CMC-Na, it is deduced that the Herschel-Bulkley method is the rheological model which best fits the experimental data.

TABLE 3

Rheological models that best predict the behavior of the studied formulations.

| | DESCRIPTION | Best rheological model | |
|---|---|---|---|
| CODE | SAMPLE | 0 days | 6 months |
| 1 | M1502 10% glycerol in refrigerator | Herschel-Bulkley | Almost Newton |
| 2 | M1502 0.4% hyaluronic acid in refrigerator | Newton | Newton |
| 3 | M1502 WITHOUT adrenalin in refrigerator | Herschel-Bulkley | Herschel-Bulkley |
| 4 | M1502 WITHOUT adrenalin room temperature | Herschel-Bulkley | Herschel-Bulkley |
| 5 | M1502 WITH adrenalin in refrigerator | Herschel-Bulkley | Herschel-Bulkley |
| 6 | M1502 WITH adrenalin room temperature | Herschel-Bulkley | Herschel-Bulkley |

TABLE 4

Rheological parameters obtained after assigning the experimental data to the rheological models.

| | Ascendant stretch | | | | | | | Descendent stretch | | | | | | |
|---|---|---|---|---|---|---|---|---|---|---|---|---|---|---|
| | $\eta$ | $\tau_0$ | $\eta_p$ | n | K | $K_1$ | $r^2$ | $\eta$ | $\tau_0$ | $\eta_p$ | n | K | $K_1$ | r |
| Newton | 1.09 | — | — | — | — | — | 0.6856 | 1.00 | — | — | — | — | — | 0.8902 |
| Bingham | — | 7.00 | 0.67 | — | — | — | 0.978 | — | 4.53 | 0.73 | — | — | — | 0.9843 |
| Ostwald de Waele | — | — | — | 0.45 | 5.27 | — | 0.9996 | — | — | — | 0.57 | 3.42 | — | 0.9998 |
| Herschel-Bulkley | — | 1.02 | — | 0.49 | — | 4.47 | 0.9999 | — | −0.25 | — | 0.56 | — | 3.59 | 0.9998 |
| Casson | — | 4.00 | — | — | — | 0.32 | 0.9948 | — | 2.09 | — | — | — | 0.43 | 0.9956 |

In Table 4, Newton: (1) $\tau = \eta \times \gamma$, Bingham: (2) $\tau = \tau_0 + \eta_p \times \gamma$, Ostwald-de Waele: (3) $\tau = k \times (\gamma)^n$, Herschel-Bulkley: (4) $\tau = \tau_0 + k_1 \times (\gamma)^n$ and Casson: (5) $\sqrt{\tau} = \sqrt{\tau_0} + k_1 \times \sqrt{\gamma}$) for the ascending and descending section.

Where $\tau$ is the shear stress, ã is the strain rate of the fluid (1/s), $T_0$ is the threshold stress required for the fluid to start moving (Pa), $\eta_p$ is the plastic viscosity (Pa·s), $\eta_O$ is zero shear viscosity (Pa·s), K is consistency (s) and n is the flow number, the different values of n indicate the behavior of the fluid. For a Newtonian fluid, n=1. If n<1, the fluid is pseudoplastic; if n>1, the fluid is a dilatant.

Optical Characterization by Means of Multiple Light Scattering

The equipment has an optical head with an infrared light source and two detectors (T and BS) running along the entire height of the sample located in the glass cell. With the data collected in relation to light intensity in Transmission (T) (backscattering) and Reflection (BS) data, more commonly referred to as "Backscattering", profiles were obtained that allowed characterizing the sample and detecting processes such as sedimentation, flocculation, coalescence, phase separation, flotation, etc. In summary, said technique allows detecting changes in size or location in the samples and allows evaluating the physical stability, preventing dilution of the formulation. Another important advantage is the capacity to detect destabilization phenomena much sooner than the human eye can and it is considered a device that predicts long-term stability, being able to detect destabilization of the formula before the conventional stability methods can. The assays were performed at 25° C. and sampling comprised 0, 30 and 90 days.

Figure 13:
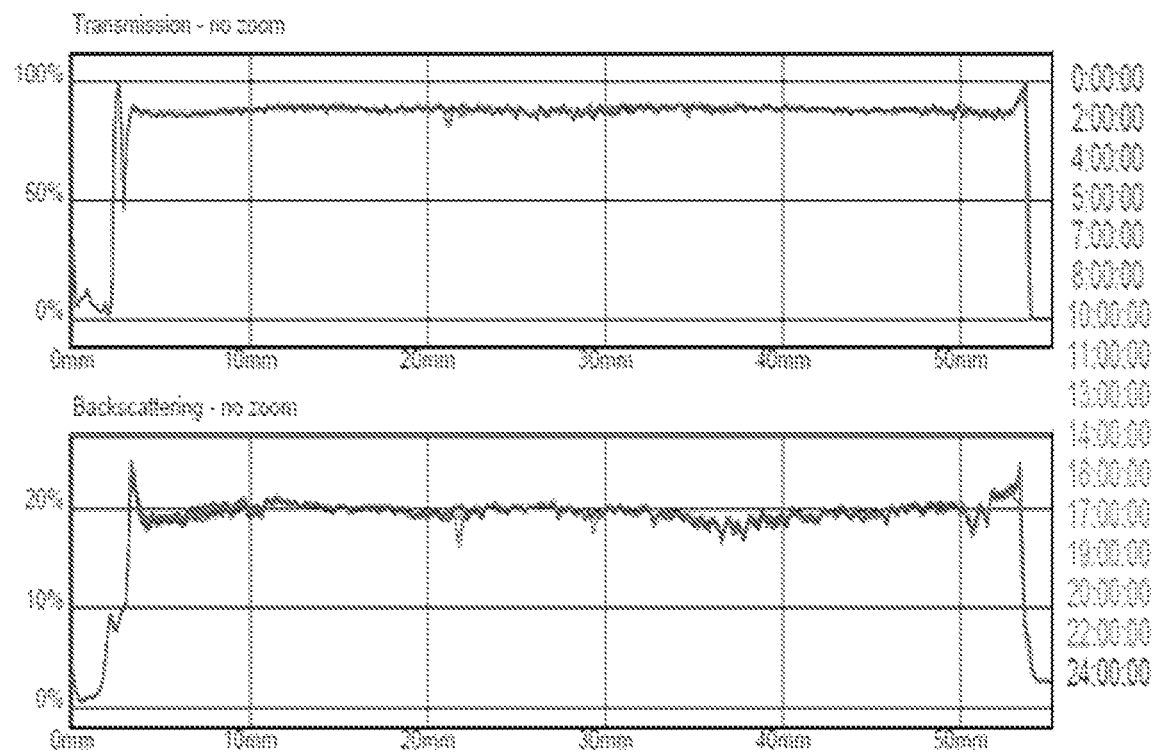
FIG. 13 shows the transmission and backscattering profiles of Formulation 3 (without adrenalin), at time 0, refrigerator.
Figure 14:
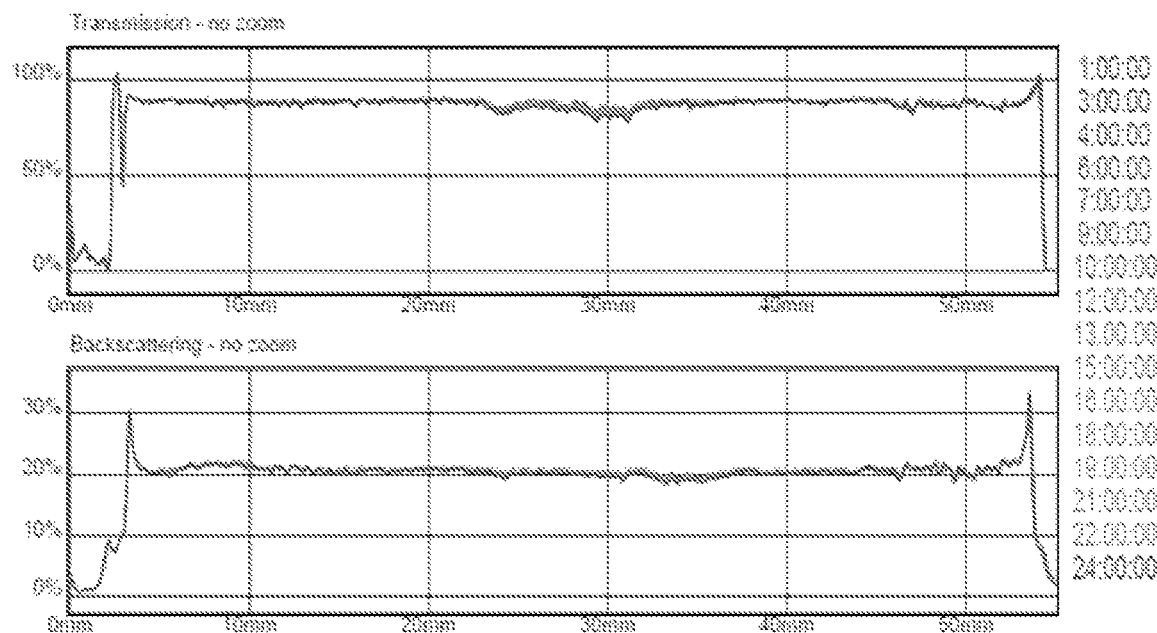
FIG. 14 shows the transmission and backscattering profiles of Formulation 3 (without adrenalin), at time 30 days, refrigerator.
Figure 15:
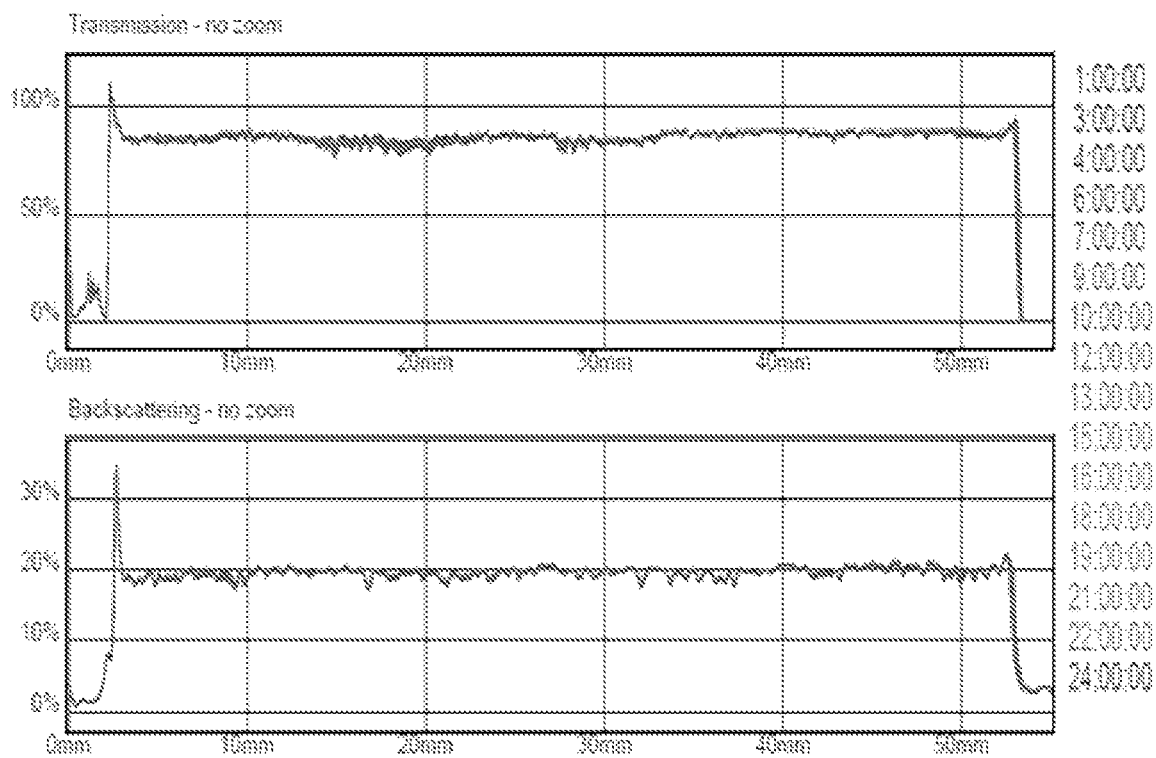
FIG. 15 shows the transmission and backscattering profiles of Formulation 4 (without adrenalin), at time 30 days, room temperature.
Figure 16:
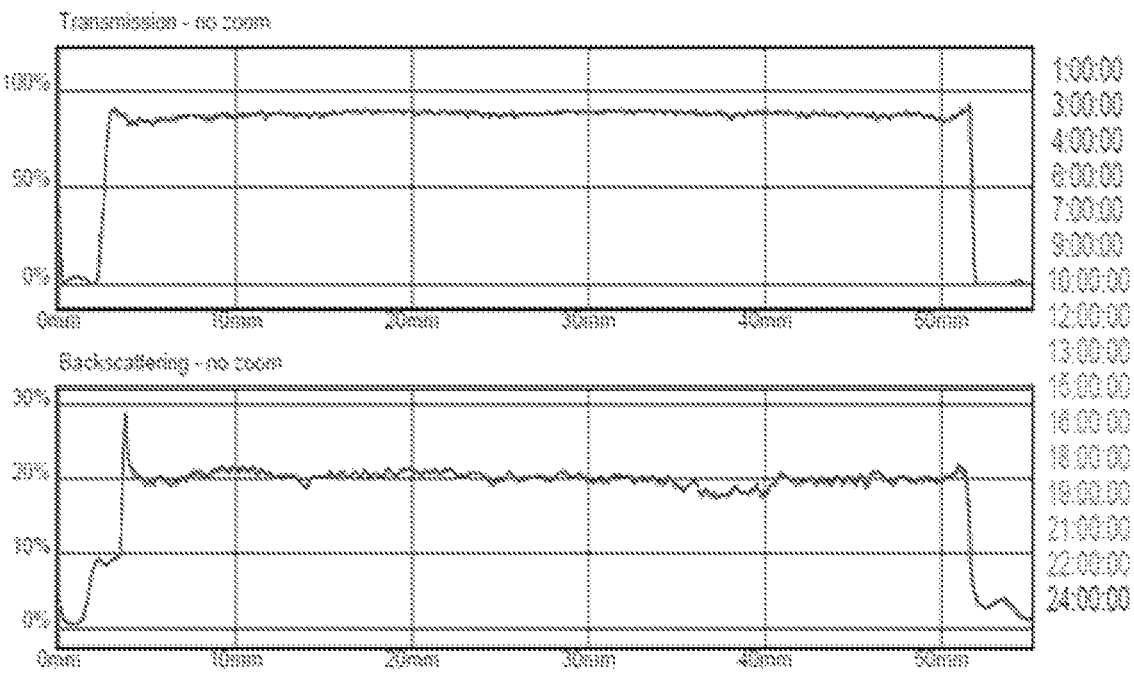
FIG. 16 shows the transmission and backscattering profiles of Formulation 5 (with adrenalin), at time 0, refrigerator.
Figure 17:
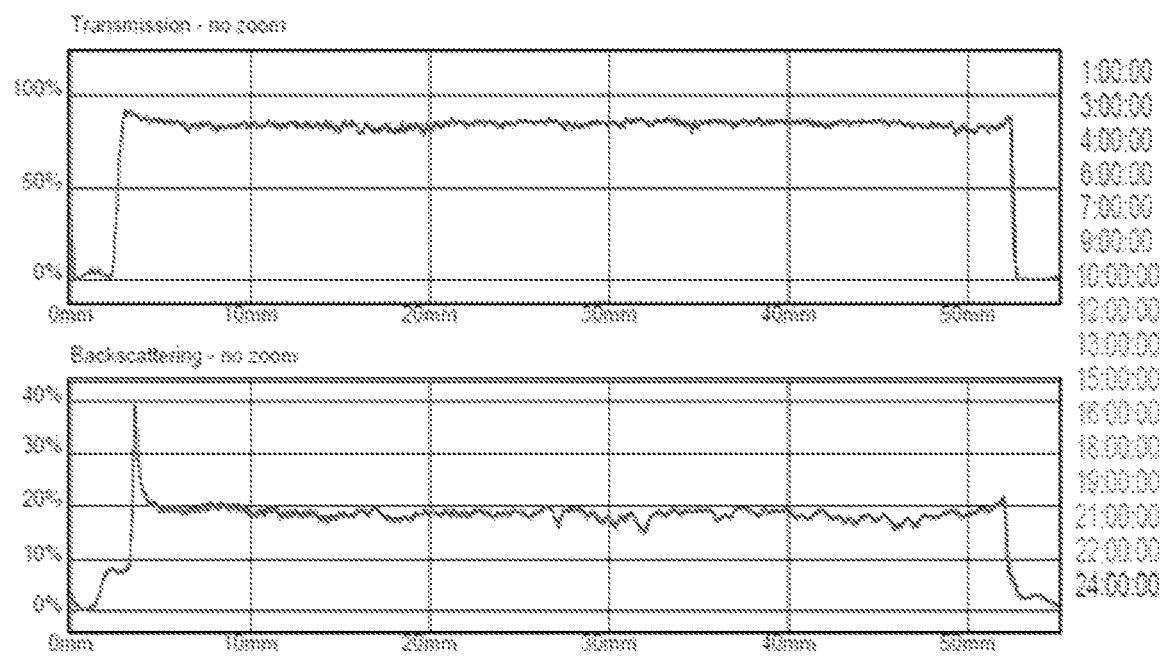
FIG. 17 shows the transmission and backscattering profiles of Formulation 5 (with adrenalin), at time 30 days, refrigerator.
Figure 18:
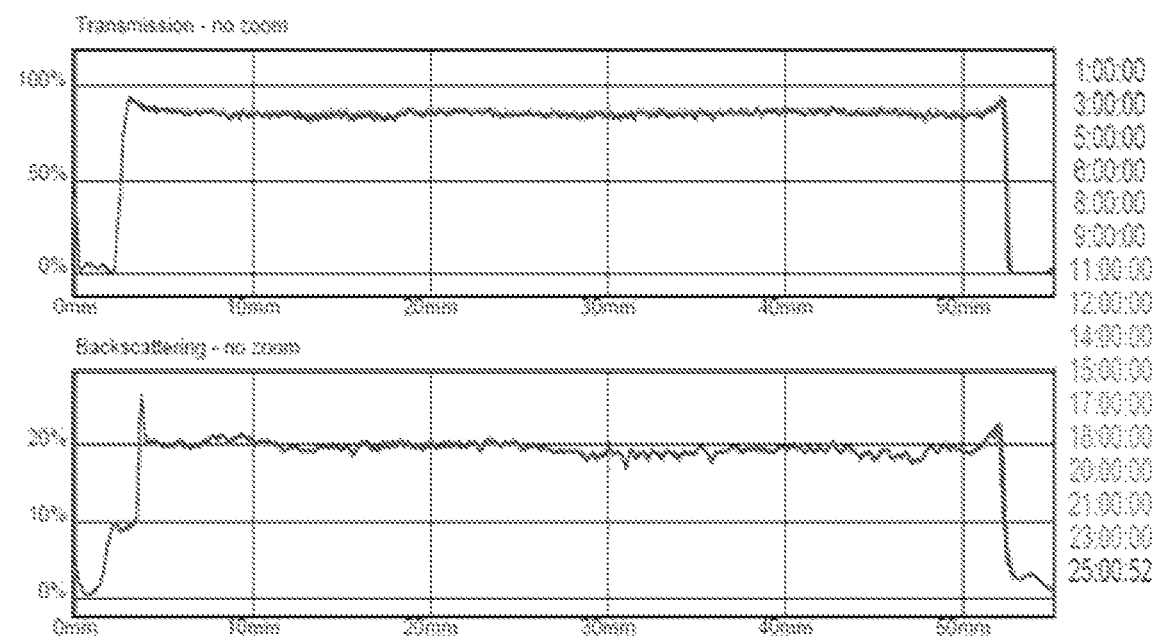
FIG. 18 shows the transmission and backscattering profiles of Formulation 5 (with adrenalin), at time 90 days, refrigerator.
Figure 19:
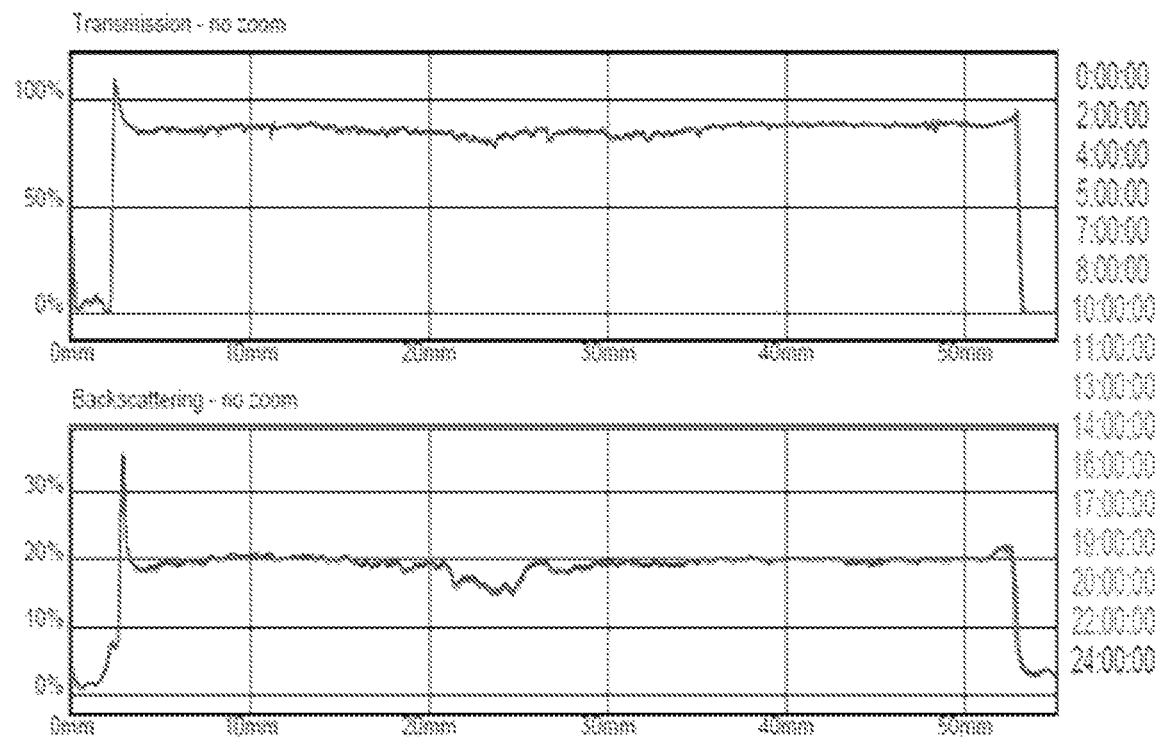
FIG. 19 shows the transmission and backscattering profiles of Formulation 6 (with adrenalin), at time 30 days, room temperature.
Figure 20:
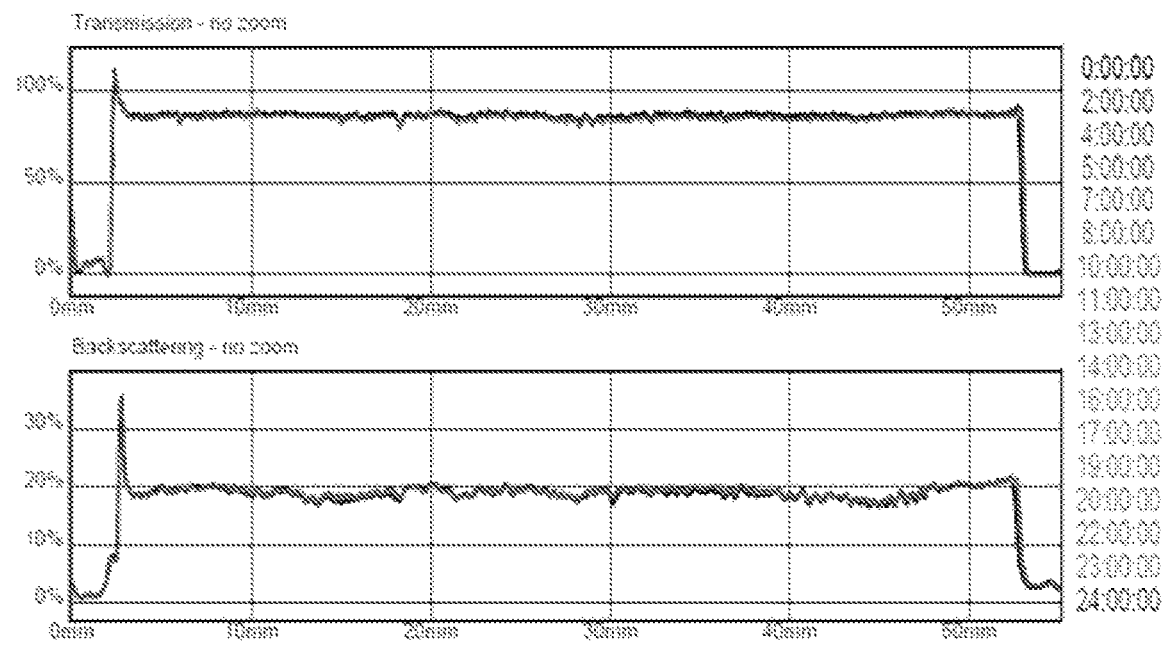
FIG. 20 shows the transmission and backscattering profiles of Formulation 6 (with adrenalin), at time 90 days, room temperature.

FIGS. 13 to 20 show the transmission and backscattering profiles of the tested formulations. In order to interpret them, it must be taken into account that the left side of the curves corresponds to the lower part of the vial, whereas the right side corresponds to the upper part. It must be specified that the region below 5 mm marks the metal base, and backscattering above 52 mm the marks the start of the sample-free surface.

When a sedimentation phenomenon occurs, the reflection signal increases over time, in the low part of the vial. When the sample experiences a creaming phenomenon, an increase occurs in the upper part of the vial. If the destabilization process occurs by means of aggregation, backscattering increases over time throughout the entire vial.

If the transmission signal has a ≤±2% deviation, it can be considered that there will not be significant differences in drop size. Variations of 10% indicate formulation instability.

The superposition of the transmission and/or reflection signal from hours 0 to 24 shows the formulation stability, indicating the absence of destabilization processes. This pattern is repeated over time and regardless of the presence of adrenalin or according to the conservation temperature. Therefore, it could be concluded that the formulations constitute homogenous dispersions.

The invention claimed is:

1. A method for the treatment of mucosal lesions, wherein said method comprises the administration of a composition by means of injection in a submucosal layer of a subject, and wherein said composition comprises:
   a. carboxymethyl cellulose at a concentration from 0.1% to 0.4%; and
   b. hyaluronic acid at a concentration from 0.001% to 0.012%.

2. The method according to claim 1, wherein said composition is administered by means of endoscopic injection.

3. The method according to claim 1, further comprising resection of a portion of the mucosa.

4. The method according to claim 3, wherein resection is an endoscopic resection of the mucosa.

5. The method according to claim 4, wherein said endoscopic resection of the mucosa is selected from the group consisting of i) endoscopic submucosal resection (EMR) and ii) endoscopic submucosal dissection (EDS).

6. The method according to claim 3, wherein said mucosa is the mucosa of the gastrointestinal tract.

7. The method according to claim 1, wherein the injection pressure is from 0.1 to 12 kgf.

8. The method according to claim 7, wherein the injection is conducted with an endoscopic injection needle with a diameter of 23G.

9. The method according to claim 1, wherein a retention time of the composition is at least 45 minutes.

10. The method according to claim 9, wherein a retention time of the composition is of 60 minutes or more.

11. The method according to claim 1, wherein the injection produces a protuberance in the submucosal layer and the mean height of the protuberance during a retention time is at least 3 mm.

12. The method according to claim 11, wherein the mean height of the protuberance is 4 mm or more.

13. The method according to claim 1, wherein said lesions of the gastrointestinal tract are tumors, polyps, or combinations thereof.

\* \* \* \* \*